(12) United States Patent
Posner et al.

(10) Patent No.: US 8,592,611 B2
(45) Date of Patent: Nov. 26, 2013

(54) TRIOXANE DIMER SULFUR COMPOUNDS

(75) Inventors: Gary H. Posner, Baltimore, MD (US); Andrew S. Rosenthal, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 403 days.

(21) Appl. No.: 13/003,869

(22) PCT Filed: Jul. 17, 2009

(86) PCT No.: PCT/US2009/051043
§ 371 (c)(1),
(2), (4) Date: Feb. 2, 2011

(87) PCT Pub. No.: WO2010/009428
PCT Pub. Date: Jan. 21, 2010

(65) Prior Publication Data
US 2011/0124603 A1 May 26, 2011

Related U.S. Application Data

(60) Provisional application No. 61/081,657, filed on Jul. 17, 2008.

(51) Int. Cl.
*C07D 493/18* (2006.01)
*A61K 31/357* (2006.01)

(52) U.S. Cl.
USPC ............ 549/348; 549/220; 514/100; 514/450

(58) Field of Classification Search
USPC ............................ 549/220, 348; 514/100, 450
See application file for complete search history.

(56) References Cited

U.S. PATENT DOCUMENTS 6,166,065 A 12/2000 Bachi et al.
7,417,156 B2 * 8/2008 Posner et al. ............... 549/348
7,632,941 B2 12/2009 Defaye et al.
2006/0142377 A1 6/2006 Posner et al.
2007/0167401 A1 7/2007 Defaye et al.

FOREIGN PATENT DOCUMENTS

WO WO 2007/067333 A2 6/2007

OTHER PUBLICATIONS

Posner et al., "Malaria-infected mice are cured by a single dose of novel artemisinin derivatives", *J. Med. Chem.*, 50(10):2516-2519 (2007).
Posner et al., "Orally active, antimalarial, anticancer, artemisinin-derived trioxane dimers with high stability and efficacy", *J. Med. Chem.*, 46(6):1060-1065 (2003).

* cited by examiner

*Primary Examiner* — Bernard Dentz
(74) *Attorney, Agent, or Firm* — DLA Piper LLP (US)

(57) ABSTRACT

The disclosure provides novel trioxane sulfur dimers having Formula I:

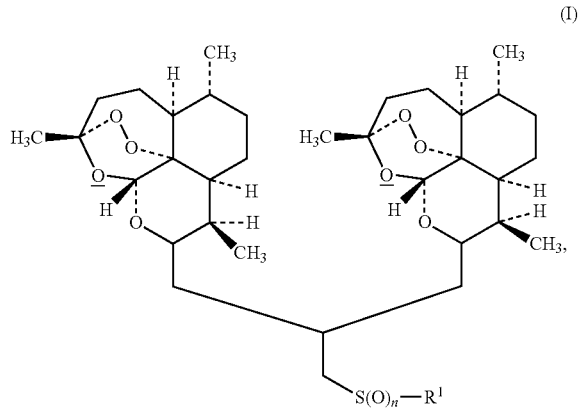

methods for their preparation, pharmaceutical compositions containing these compounds, and methods for treating cancer, proliferative disorders, and/or malaria using these compounds and/or compositions.

21 Claims, No Drawings

TRIOXANE DIMER SULFUR COMPOUNDS

CROSS REFERENCE TO RELATED APPLICATIONS

This application is a 35 USC §371 National Stage application of International Application No. PCT/US2009/051043 filed Jul. 17, 2009, now pending; which claims the benefit under 35 USC §119(e) to U.S. Application Ser. No. 61/081,657 filed Jul. 17, 2008, now expired. The disclosure of each of the prior applications is considered part of and is incorporated by reference in the disclosure of this application.

FIELD OF THE DISCLOSURE

The disclosure provides novel trioxane dimer sulfur compounds, methods for their preparation, pharmaceutical compositions containing these compounds, and methods for treating cancer, proliferative disorders, and/or malaria using these compounds and/or compositions.

BACKGROUND OF THE DISCLOSURE

Each year approximately 200-300 million people experience a malarial illness in which over 1 million individuals die. In patients with severe and complicated disease, the mortality rate is between 20 and 50%. *Plasmodium* is the genus of protozoan parasites that is responsible for all cases of human malaria, and *Plasmodium falciparum* is the species of parasite that is responsible for the vast majority of fatal malaria infections. Malaria has traditionally been treated with quinolines such as chloroquine, quinine, mefloquine, and primaquine and with antifolates such as sulfadoxine-pyrimethamine. Unfortunately, most *P. falciparum* strains have now become resistant to chloroquine, and some strains, such as those found in Southeast Asia, have also developed resistance to mefloquine and halofantrine. Multidrug resistance to this species of parasites is also developing in Africa.

The endoperoxides are a promising class of antimalarial drugs that may meet the dual challenges posed by drug-resistant parasites and the rapid progression of malarial illness. The first generation endoperoxides include natural artemisinin and several synthetic derivatives. *Artemisia annua* L., also known as qinghao or sweet wormwood, is a pervasive weed that has been used for many centuries in Chinese traditional medicine as a treatment for fever and malaria. In 1972 Chinese chemists isolated from the leafy portions of the plant the substance responsible for its reputed medicinal action. This crystalline compound, called qinghaosu, also referred to as QHS or artemisinin, is a sesquiterpene lactone with an internal peroxide linkage as shown below:

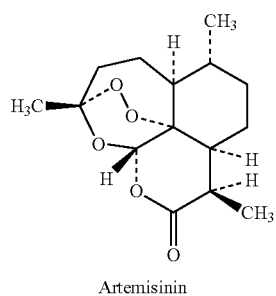 [SMILES: C[C@@H]1CC[C@H]2[C@@H](C)C(=O)O[C@@H]3O[C@]4(C)CC[C@@H]1[C@]32OO4]

Artemisinin

Artemisinin is a member of the amorphane subgroup of cadinenes. This compound was the subject of a 1979 study conducted by the Qinghaosu Antimalarial Coordinating Research Group involving the treatment of 2099 cases of malaria (*P. vivax* and *P. falciparum* in a ratio of about 3:1) with different dosage forms, leading to the clinical cure of all patients (Qinghaosu Antimalarial Coordinating Research Group, Chin. Med. J., 92:811 (1979)). Since that time artemisinin has been used successfully in many thousand malaria patients throughout the world including those infected with both chloroquine-sensitive and chloroquine-resistant strains of *P. falciparum*. Assay of artemisinin against *P. falciparum* in vitro revealed that its potency is comparable to that of chloroquine in two Hanian strains (Z. Ye, et al., J. Trad. Chin. Med., 3:95 (1983)) and of mefloquine in the Camp (chloroquine-susceptible) and Smith (chloroquine-resistant) strains (D. L. Klayman, et al., J. Nat. Prod., 47:715 (1984)).

Although artemisinin is effective at suppressing the parasitemias of *P. vivax* and *P. falciparum*, the problems encountered with recrudescence, and the compound's insolubility in water, led scientists to modify artemisinin chemically, a difficult task because of the chemical reactivity of the peroxide linkage which is believed to be an essential moiety for antimalarial activity. These modifications include the reduction of artemisinin to dihydroartemisinin or DHQHS, in which the lactone group is converted to a lactol (hemiacetal) function, and which has similar properties to artemisinin. Dihydroartemisinin may also be converted to a large number of other derivatives, such as artemether, arteether, sodium artesunate, artelinic acid, sodium artelinate, and dihydroartemisinin (R. Haynes, Transactions of the Royal Society of Tropical Medicine and Hygiene, 88(1): S1/23-S1/26 (1994); Brossi, et al., 1988; M. Cao, et al., Chem. Abstr., 100:34720k (1984)).

Other rational design of structurally simpler analogs of artemisinin has led to the synthesis of various trioxanes, some of which possess excellent antimalarial activity. For example, Posner, G. H., et al., reported the chemistry and biology of a series of new structurally simple, easily prepared, racemic 1,2,4-trioxanes as disclosed in U.S. Pat. No. 5,225,437; U.S. patent application Ser. No. 10/529,513; and in Posner, G. H., et al., J. Med. Chem., 35:2459-2467 (1992), the disclosure of each of which are hereby incorporated herein by reference in their entirety for all purposes. Jung, M., et al., has also reported on the antitumor activity of dimeric deoxyartemisinin derivatives with alkylamide and sulfur linkers of various lengths and flexibility (Journal of Medicinal Chemistry, 2003, Vol. 46, No. 6, 987-994). The complete chemical synthesis of artemisinin and a variety of other derivatives is reviewed by Sharma, R. P., et al., Heterocycles, 32(8):1593-1638 (1991), and is also incorporated herein by reference. Unfortunately, most C-10 acetal derivatives are often unstable in water, i.e. they are easily hydrolyzed. Therefore making hydrolytically stable C-10 non-acetal carba-derivatives has become a high priority.

Since the isolation of artemisinin, there has been a concerted effort by investigators to study other therapeutic applications of artemisinin and its derivatives. The National Institutes of Health reported that artemisinin is inactive against P388 leukemia (NCI Report on NSC 369397, tested on 25 Oct. 1983). Later anticancer studies that have been conducted on cell line panels consisting of 60 lines organized into nine, disease-related subpanels including leukemia, non-small-cell lung cancer, colon, CNS, melanoma, ovarian, renal, prostate and breast cancers, further confirm that artemisinin displays modest anticancer activity.

While artemisinin and its related derivatives demonstrate zero to slight antiproliferative and antitumor activity, it has been discovered that a class of artemisinin dimer compounds exhibits antiproliferative and antitumor activities that are, in vitro, equivalent to or greater than known antiproliferative and antitumor agents (U.S. Pat. No. 5,677,468 also incorporated herein by reference in its entirety for all purposes). Unfortunately, while the in vitro results of these artemisinin compounds are encouraging, these compounds do not appear to have as significant antitumor activity on the treatment of tumor cells in mice.

There is still a need, therefore, to develop stable artemisinin derivatives and structural analogs thereof having antimalarial, anticancer, antiproliferative, and antitumor activities that are equivalent to or greater than those of known antimalarial, anticancer, antiproliferative and antitumor agents, respectively.

SUMMARY OF THE DISCLOSURE

The disclosure provides a novel class of artemisinin related dimers having antitumor and antimalarial activities. More specifically, the disclosure provides a class of trioxane dimer sulfur compounds having antitumor and antimalarial activities, which are considerably more stable toward hydrolysis than artemether and related C-10 ethers and esters, and which may be used clinically as chemotherapeutic antitumor and antimalarial drugs.

Thus, in one embodiment, the disclosure provides a compound of Formula I:

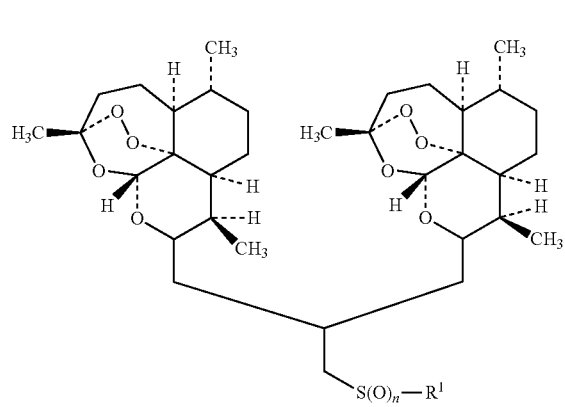

I or a pharmaceutically acceptable salt or solvate thereof, wherein:

n is independently an integer from 0 to 2;

$R^1$ is independently hydrogen, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, or substituted or unsubstituted heteroarylalkyl, wherein $R^1$ is optionally independently substituted with 1 to 5 $R^2$ groups;

$R^2$ is independently hydrogen, halogen, nitro, cyano, hydroxyl, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, substituted or unsubstituted heteroarylalkyl, —(CH$_2$)$_j$CN, —(CH$_2$)$_j$OR$^3$, —(CH$_2$)$_q$O(CH$_2$)$_j$OR$^3$, —(CH$_2$)$_q$O(CH$_2$)$_t$O(CH$_2$)OR$^3$, —(CH$_2$)$_q$O(CH$_2$)$_t$O(CH$_2$)$_u$ O(CH$_2$)$_j$OR$^3$, —(CH$_2$)$_j$C(O)R$^3$, —(CH$_2$)$_j$C(O)OR$^3$, —(CH$_2$)$_j$OC(O)R$^3$, —(CH$_2$)$_j$NR$^4$R$^5$, —(CH$_2$)$_j$C(O)NR$^4$R$^5$, —(CH$_2$)$_j$OC(O)NR$^4$R$^5$, —(CH$_2$)$_j$NR$^6$C(O)R$^3$, —(CH$_2$)$_j$ NR$^6$C(O)OR$^3$, —(CH$_2$)$_j$NR$^6$C(O)NR$^4$R$^5$, —(CH$_2$)$_j$S(O)$_m$ R$^7$, —(CH$_2$)$_j$S(O)$_2$NR$^4$R$^5$, —(CH$_2$)$_j$NR$^6$S(O)$_2$R$^7$, or —(CH$_2$)$_j$OP(O)(OR$^7$)$_2$, wherein q is independently an integer from 0 to 20, and j, t, and u are each independently an integer from 0 to 6, and each m is independently an integer from 0 to 2, wherein $R^2$ is optionally independently substituted with 1 to 5 $R^8$ groups;

$R^3$, $R^4$, $R^5$, $R^6$, and $R^7$ are each independently hydrogen, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, or substituted or unsubstituted heteroarylalkyl, or $R^3$, $R^6$, and $R^7$ are as described above, and $R^4$ and $R^5$, together with the N atom to which they are attached, form substituted or unsubstituted heterocycloalkyl, or substituted or unsubstituted heteroaryl, wherein $R^3$, $R^4$, $R^5$, $R^6$, and $R^7$ are each optionally independently substituted with 1 to 5 $R^8$ groups; and $R^8$ is independently halogen, hydroxyl, cyano, nitro, alkyl, perfluoroalkyl, oxo, NH$_2$, NH(alkyl), N(alkyl)$_2$, O-alkyl, S-alkyl, aryl, arylalkyl, heteroaryl or heteroarylalkyl.

In other embodiments, the disclosure provides methods for preparing a compound of Formula I, pharmaceutical compositions containing these compounds, and methods for treating cancer and/or malaria using these compounds and/or compositions.

Additional objects, advantages and novel features of the disclosure shall be set forth in part in the description and examples that follow, and in part will become apparent to those skilled in the art upon examination of the following specification or may be learned by the practice of the disclosure. The objects and advantages of the disclosure may be realized and attained by means of the instrumentalities, combinations, compositions, and methods particularly pointed out in the appended claims.

DETAILED DESCRIPTION OF THE DISCLOSURE

Definitions

Abbreviations used herein have their conventional meaning within the chemical and biological arts.

Where substituent groups, e.g., linking groups, are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O) NR— is equivalent to —NRC(=O)O—, and the like.

The term "alkyl," by itself or as part of another substituent, means, unless otherwise stated, a straight (i.e. unbranched) or branched chain, acyclic or cyclic hydrocarbon group, or combination thereof, which may be fully saturated, mono- or polyunsaturated and can include di- and multivalent groups, having the number of carbon atoms designated (i.e. C$_1$-C$_{10}$ means one to ten carbons). Examples of saturated hydrocarbon groups include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. Also included in the definition of alkyl and cycloalkyl are bicyclic ring structures such as norbornyl and adamantyl and the like, and fused ring systems such as dihydro- and tetrahydronaphthalene, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl".

The term "alkylene" by itself or as part of another substituent means a divalent group derived from an alkyl, as exemplified, but not limited, by —$CH_2CH_2CH_2CH_2$—, —$CH_2CH$=$CHCH_2$—, —$CH_2C$≡$CCH_2$—, —$CH_2CH_2CH(CH_2CH_2CH_3)CH_2$—. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

Similarly, the term "heteroalkylene" by itself or as part of another substituent means a divalent group derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxo, arylthioxo, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

The term "oxo" as used herein means an oxygen that is double bonded to a carbon atom.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R")=NR'", —S(O)R', —S(O)$_2$R', —S(O)$_2$NR'R", —NRSO$_2$R', —CN and —NO$_2$ in a number ranging from zero to (2 m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR'", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro(C$_1$-C$_4$)alkyl, in a number ranging from zero to the total number of open valences on aromatic ring system; and where R', R", R'" and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R'" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$), —B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

An "aminoalkyl" as used herein refers to an amino group covalently bound to an alkylene linker. The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and each substituted or unsubstituted heterocycloalkyl is a substituted or unsubstituted 5 to 7 membered heterocycloalkyl.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^{3}$H), iodine-125 ($^{125}$I) or carbon-14 ($^{14}$C). All isotopic variations of the compounds of the present disclosure, whether radioactive or not, are encompassed within the scope of the present disclosure.

The term "pharmaceutically acceptable salts" is meant to include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" in reference to a particular disease includes prevention of the disease.

The symbol ⁓ denotes the point of attachment of a moiety to the remainder of the molecule.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

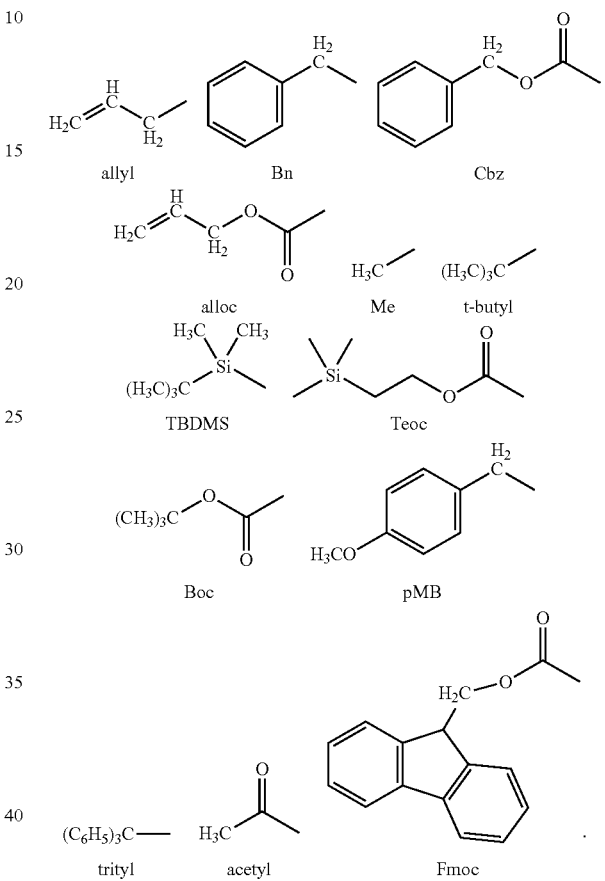

Trioxane Dimer Sulfur Compounds

We provide herein the design, synthesis and biological evaluation of a new series of trioxane sulfur dimers. Previously, monomeric 1; 2,4-trioxanes such as natural artemisinin I and derivatives thereof, have shown both anticancer activity as well as antimalarial activity. For example, monomeric 1,2,4-trioxanes such as dihydroartemisinin (DHA):

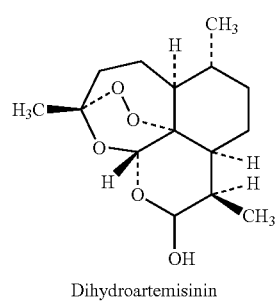

Dihydroartemisinin has shown anticancer activity against human HeLa cervical cancer cells in vitro ($IC_{50}$=5-10 μM). The new class of trioxane sulfur dimer compounds disclosed herein, surprisingly, possesses improved activity and/or selectivity for treating cancer and/or malaria.

Also provided are trioxane sulfur dimers that have in vitro and in vivo anticancer, antiproliferative and antitumor activity, as well as in vitro and in vivo antimalarial activity. These new dimers show selective anticancer activity and have longer lasting antimalarial activity than does monomeric artemisinin and its derivatives. The stability and hydrophobicity of the disclosed trioxane sulfur dimers also makes them excellent candidates for not only systemic but also topical application, a route of administration which would permit also high dosaging without the risk of systemic side effects.

The synthesis of the disclosed trioxane sulfur dimers is outlined below in Scheme I:

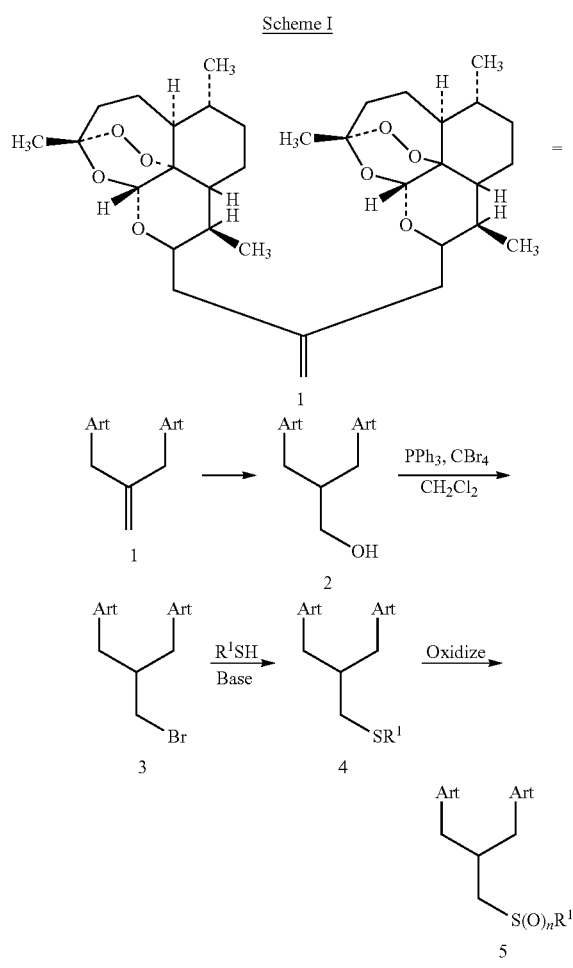

In Scheme I, the olefinic trioxane dimer 1 and primary alcohol 2 may be prepared according to the procedures in U.S. patent application Ser. No. 10/529,513 previously incorporated herein by reference. Thus, treatment of alcohol 2 under bromination conditions (PPh$_3$, CBr$_4$, CH$_2$Cl$_2$ at room temperature), provided the corresponding primary bromide 3. Other bromination conditions are known to those of skill in the art and are easily employed. Alternatively, other leaving groups, including other halogens (chloride and iodide), tosylate, mesylate or triflate groups, may also be easily prepared and utilized by those of skill in the art. Bromide 3 was reacted with sulfide compound 4 (HSR$^1$, base) to provide the new sulfide compound 4. Appropriate bases useful in this reaction include, but are not limited to, alkali metal bases such as sodium hydride and potassium hydride, and organic nitrogen bases such as 1,8-diazabicyclo[5.4.0]undec-7-ene (DBU), triethylamine, diphenylamine, pyridine, and the like. Finally, controlled oxidation of sulfide 4 using 1 or 2 equivalents of an oxidizing agent, provides the sulfoxide and/or sulfone compound 5, respectively. Appropriate oxidizing agents include, but are not limited to, mCPBA, dimethyldioxirane, and Oxone®.

Thus, in one aspect the disclosure provides a compound of Formula I:

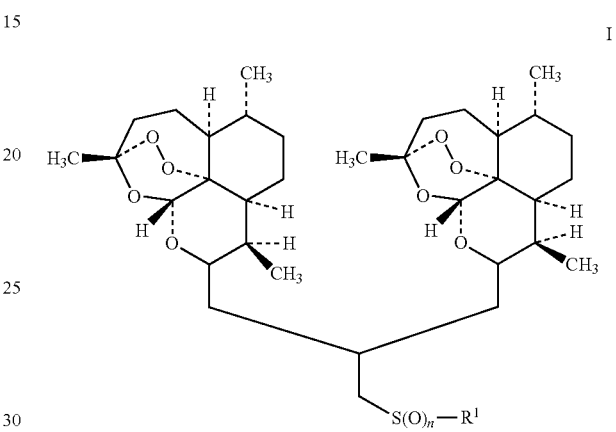

or a pharmaceutically acceptable salt or solvate thereof, wherein:

n is independently an integer from 0 to 2;

R$^1$ is independently hydrogen, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, or substituted or unsubstituted heteroarylalkyl, wherein R$^1$ is optionally independently substituted with 1 to 5 R$^2$ groups;

R$^2$ is independently hydrogen, halogen, nitro, cyano, hydroxyl, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, substituted or unsubstituted heteroarylalkyl, —(CH$_2$)$_j$CN, —(CH$_2$)$_j$OR$^3$, —(CH$_2$)$_q$O(CH$_2$)$_j$OR$^3$, —(CH$_2$)$_q$O(CH$_2$)$_t$O(CH$_2$)$_j$OR$^3$, —(CH$_2$)$_q$O(CH$_2$)$_t$O(CH$_2$)$_u$O(CH$_2$)$_j$OR$^3$, —(CH$_2$)$_j$C(O)R$^3$, —(CH$_2$)$_j$C(O)OR$^3$, —(CH$_2$)$_j$OC(O)R$^3$, —(CH$_2$)$_j$NR$^4$R$^5$, —(CH$_2$)$_j$C(O)NR$^4$R$^5$, —(CH$_2$)$_j$OC(O)NR$^4$R$^5$, —(CH$_2$)$_j$NR$^6$C(O)R$^3$, —(CH$_2$)$_j$NR$^6$C(O)OR$^3$, —(CH$_2$)$_j$NR$^6$C(O)NR$^4$R$^5$, —(CH$_2$)$_j$S(O)$_m$R$^7$, —(CH$_2$)$_j$S(O)$_2$NR$^4$R$^5$, —(CH$_2$)$_j$NR$^6$S(O)$_2$R$^7$, or —(CH$_2$)$_j$OP(O)(OR$^7$)$_2$, wherein q is independently an integer from 0 to 20, and j, t, and u are each independently an integer from 0 to 6, and each m is independently an integer from 0 to 2, wherein R$^2$ is optionally independently substituted with 1 to 5 R$^8$ groups;

R$^3$, R$^4$, R$^5$, R$^6$, and R$^7$ are each independently hydrogen, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, or substituted or unsubstituted heteroarylalkyl, or $R^3$, $R^6$, and $R^7$ are as described above, and $R^4$ and $R^5$, together with the N atom to which they are attached, form substituted or unsubstituted heterocycloalkyl, or substituted or unsubstituted heteroaryl, wherein $R^3$, $R^4$, $R^5$, $R^6$, and $R^7$ are each optionally independently substituted with 1 to 5 $R^8$ groups; and $R^8$ is independently halogen, hydroxyl, cyano, nitro, alkyl, perfluoroalkyl, oxo, $NH_2$, NH(alkyl), N(alkyl)$_2$, O-alkyl, S-alkyl, aryl, arylalkyl, heteroaryl or heteroarylalkyl.

In another aspect, the disclosure provides a compound of Formula I, wherein:

n is independently 2;

$R^1$ is independently substituted or unsubstituted ($C_1$-$C_{20}$) alkyl, substituted or unsubstituted ($C_1$-$C_{20}$)heteroalkyl, substituted or unsubstituted ($C_3$-$C_7$)cycloalkyl, substituted or unsubstituted ($C_3$-$C_7$)heterocycloalkyl, substituted or unsubstituted phenyl, substituted or unsubstituted biphenyl, substituted or unsubstituted naphthyl, substituted or unsubstituted benzyl, substituted or unsubstituted pyrrolyl, substituted or unsubstituted pyrazolyl, substituted or unsubstituted imidazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzimidazolyl, substituted or unsubstituted benzofuryl, substituted or unsubstituted benzothienyl, substituted or unsubstituted benzoxazolyl, substituted or unsubstituted benzoisooxazolyl, substituted or substituted benzthiazolyl, substituted or unsubstituted quinolinyl, substituted or unsubstituted isoquinolinyl, substituted or unsubstituted phthalazinyl, substituted or unsubstituted quinazolinyl, or substituted or unsubstituted quinoxalinyl;

$R^2$ is independently hydrogen, halogen, nitro, cyano, hydroxyl, substituted or unsubstituted ($C_1$-$C_6$)alkyl, substituted or unsubstituted ($C_1$-$C_6$)heteroalkyl, perfluoroalkyl, substituted or unsubstituted ($C_3$-$C_7$)cycloalkyl, substituted or unsubstituted ($C_3$-$C_7$)heterocycloalkyl, substituted or unsubstituted phenyl, substituted or unsubstituted biphenyl, substituted or unsubstituted naphthyl, substituted or unsubstituted benzyl, substituted or unsubstituted pyrrolyl, substituted or unsubstituted pyrazolyl, substituted or unsubstituted imidazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzimidazolyl, substituted or unsubstituted benzofuryl, substituted or unsubstituted benzothienyl, substituted or unsubstituted benzoxazolyl, substituted or unsubstituted benzoisooxazolyl, substituted or unsubstituted benzthiazolyl, substituted or unsubstituted quinolinyl, substituted or unsubstituted isoquinolinyl, substituted or unsubstituted phthalazinyl, substituted or unsubstituted quinazolinyl, substituted or unsubstituted quinoxalinyl, —(CH$_2$)$_j$CN, —(CH$_2$)$_j$OR$^3$, —(CH$_2$)$_q$O(CH$_2$)$_j$OR$^3$, —(CH$_2$)$_q$O(CH$_2$)$_j$O(CH$_2$)$_j$OR$^3$, —(CH$_2$)$_q$O(CH$_2$)$_j$O(CH$_2$)$_u$O(CH$_2$)$_j$OR$^3$, —(CH$_2$)$_j$C(O)R$^3$, —(CH$_2$)$_j$C(O)OR$^3$, —(CH$_2$)$_j$OC(O)R$^3$, —(CH$_2$)$_j$NR$^4$R$^5$, —(CH$_2$)$_j$C(O)NR$^4$R$^5$, —(CH$_2$)$_j$OC(O)NR$^4$R$^5$, —(CH$_2$)$_j$NR$^6$C(O)R$^3$, —(CH$_2$)$_j$NR$^6$C(O)OR$^3$, —(CH$_2$)$_j$NR$^6$C(O)NR$^4$R$^5$, —(CH$_2$)$_j$S(O)$_m$R$^7$, —(CH$_2$)$_j$S(O)$_2$NR$^4$R$^5$, —(CH$_2$)$_j$NR$^6$S(O)$_2$R$^7$, or —(CH$_2$)$_j$OP(O)(OR$^7$)$_2$;

$R^3$, $R^4$, $R^5$, $R^6$, and $R^7$ are each independently hydrogen, substituted or unsubstituted ($C_1$-$C_6$)alkyl, substituted or unsubstituted ($C_1$-$C_6$)heteroalkyl, perfluoroalkyl, substituted or unsubstituted ($C_3$-$C_7$)cycloalkyl, substituted or unsubstituted ($C_3$-$C_7$)heterocycloalkyl, substituted or unsubstituted phenyl, substituted or unsubstituted biphenyl, substituted or unsubstituted naphthyl, substituted or unsubstituted benzyl, substituted or unsubstituted pyrrolyl, substituted or unsubstituted pyrazolyl, substituted or unsubstituted imidazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzimidazolyl, substituted or unsubstituted benzofuryl, substituted or unsubstituted benzothienyl, substituted or unsubstituted benzoxazolyl, substituted or unsubstituted benzoisooxazolyl, substituted or unsubstituted benzthiazolyl, substituted or unsubstituted quinolinyl, substituted or unsubstituted isoquinolinyl, substituted or unsubstituted phthalazinyl, substituted or unsubstituted quinazolinyl, or substituted or unsubstituted quinoxalinyl, or $R^3$, $R^6$, and $R^7$ are as described above, and $R^4$ and $R^5$, together with the N atom to which they are attached, form substituted or unsubstituted pyrrolidinyl, substituted or unsubstituted imidazolidinyl, substituted or unsubstituted piperidinyl, substituted or unsubstituted piperazinyl, substituted or unsubstituted morpholinyl, substituted or unsubstituted thiomorpholinyl, substituted or unsubstituted pyrrolyl, or substituted or unsubstituted imidazolyl; and $R^8$ is independently halogen, hydroxyl, cyano, nitro, perfluoroalkyl, oxo, $NH_2$, NH(($C_1$-$C_6$)alkyl), N(($C_1$-$C_6$)alkyl)$_2$, O($C_1$-$C_6$)alkyl, S($C_1$-$C_6$)alkyl, phenyl, biphenyl, naphthyl, benzyl, pyrrolyl, pyrazolyl, imidazolyl, furyl, thienyl, oxazolyl, isooxazolyl, thiazolyl, pyridinyl, pyridazinyl, pyrimidinyl, pyrazinyl, indolyl, indazolyl, benzimidazolyl, benzofuryl, benzothienyl, benzoxazolyl, benzoisooxazolyl, benzthiazolyl, quinolinyl, isoquinolinyl, phthalazinyl, quinazolinyl, or quinoxalinyl.

In another aspect, the disclosure provides a compound of Formula I, wherein:

$R^1$ is independently substituted or unsubstituted ($C_1$-$C_{20}$) alkyl; and $R^2$ is independently hydrogen, halogen, nitro, cyano, hydroxyl, substituted or unsubstituted ($C_1$-$C_6$)alkyl, substituted or unsubstituted ($C_1$-$C_6$)heteroalkyl, perfluoroalkyl, substituted or unsubstituted ($C_3$-$C_7$)cycloalkyl, or substituted or unsubstituted ($C_3$-$C_7$)heterocycloalkyl.

In another aspect, the disclosure provides a compound of Formula I, wherein:

$R^1$ is independently substituted or unsubstituted ($C_1$-$C_{20}$) alkyl; and $R^2$ is independently substituted or unsubstituted phenyl, substituted or unsubstituted biphenyl, substituted or unsubstituted naphthyl, substituted or unsubstituted benzyl, substituted or unsubstituted pyrrolyl, substituted or unsubstituted pyrazolyl, substituted or unsubstituted imidazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzimidazolyl, substituted or unsubstituted benzofuryl, substituted or unsubstituted benzothienyl, substituted or unsubstituted benzoxazolyl, substituted or unsubstituted benzoisooxazolyl, substituted or unsubstituted benzthiazolyl, substituted or unsubstituted quinolinyl, substituted or unsubstituted isoquinolinyl, substituted or unsubstituted phthalazinyl, substituted or unsubstituted quinazolinyl, or substituted or unsubstituted quinoxalinyl.

In another aspect, the disclosure provides a compound of Formula I, wherein:

$R^1$ is independently substituted or unsubstituted $(C_1-C_{20})$ alkyl; and $R^2$ is independently —$(CH_2)_j$CN, —$(CH_2)_j$OR$^3$, —$(CH_2)_q$O$(CH_2)_j$OR$^3$, —$(CH_2)_q$O$(CH_2)_t$O$(CH_2)_j$OR$^3$, —$(CH_2)_q$O$(CH_2)_t$O$(CH_2)_u$O$(CH_2)_j$OR$^3$, —$(CH_2)_j$C(O)R$^3$, —$(CH_2)_j$C(O)OR$^3$, —$(CH_2)_j$OC(O)R$^3$, —$(CH_2)_j$NR$^4$R$^5$, —$(CH_2)_j$C(O)NR$^4$R$^5$, —$(CH_2)_j$OC(O)NR$^4$R$^5$, —$(CH_2)_j$NR$^6$C(O)R$^3$, —$(CH_2)_j$NR$^6$C(O)OR$^3$, —$(CH_2)_j$NR$^6$C(O)NR$^4$R$^5$, —$(CH_2)_j$S(O)$_m$R$^7$, —$(CH_2)_j$S(O)$_2$NR$^4$R$^5$, —$(CH_2)_j$NR$^6$S(O)$_2$R$^7$, or —$(CH_2)_j$OP(O)(OR$^7$)$_2$.

In another aspect, the disclosure provides a compound of Formula I, wherein $R^2$ is independently —$(CH_2)_j$OR$^3$, —$(CH_2)_q$O$(CH_2)_j$OR$^3$, —$(CH_2)_q$O$(CH_2)_t$O$(CH_2)_j$OR$^3$, —$(CH_2)_q$O$(CH_2)_t$O$(CH_2)_u$O$(CH_2)_j$OR$^3$.

In another aspect, the disclosure provides a compound of Formula I, wherein $R^2$ is independently —$(CH_2)_j$OR$^3$, —$(CH_2)_q$O$(CH_2)_j$OR$^3$, —$(CH_2)_q$O$(CH_2)_t$O$(CH_2)_j$OR$^3$, —$(CH_2)_q$O$(CH_2)_t$O$(CH_2)_u$O$(CH_2)_j$OR$^3$; and $R^3$ is hydrogen.

In another aspect, the disclosure provides a compound of Formula I, wherein:

$R^1$ is independently substituted or unsubstituted phenyl; and $R^2$ is independently hydrogen, halogen, nitro, cyano, hydroxyl, substituted or unsubstituted $(C_1-C_6)$alkyl, substituted or unsubstituted $(C_1-C_6)$heteroalkyl, perfluoroalkyl, substituted or unsubstituted $(C_3-C_7)$cycloalkyl, substituted or unsubstituted $(C_3-C_7)$heterocycloalkyl.

In another aspect, the disclosure provides a compound of Formula I, wherein:

$R^1$ is independently substituted or unsubstituted phenyl; and $R^2$ is independently substituted or unsubstituted phenyl, substituted or unsubstituted biphenyl, substituted or unsubstituted naphthyl, substituted or unsubstituted benzyl, substituted or unsubstituted pyrrolyl, substituted or unsubstituted pyrazolyl, substituted or unsubstituted imidazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzimidazolyl, substituted or unsubstituted benzofuryl, substituted or unsubstituted benzothienyl, substituted or unsubstituted benzoxazolyl, substituted or unsubstituted benzoisooxazolyl, substituted or unsubstituted benzthiazolyl, substituted or unsubstituted quinolinyl, substituted or unsubstituted isoquinolinyl, substituted or unsubstituted phthalazinyl, substituted or unsubstituted quinazolinyl, or substituted or unsubstituted quinoxalinyl.

In another aspect, the disclosure provides a compound of Formula I, wherein:

$R^1$ is independently substituted or unsubstituted phenyl; and $R^2$ is independently —$(CH_2)_j$CN, —$(CH_2)_j$OR$^3$, —$(CH_2)_q$O$(CH_2)_j$OR$^3$, —$(CH_2)_q$O$(CH_2)_t$O$(CH_2)_j$OR$^3$, —$(CH_2)_q$O$(CH_2)_t$O$(CH_2)_u$O$(CH_2)_j$OR$^3$, —$(CH_2)_j$C(O)R$^3$, —$(CH_2)_j$C(O)OR$^3$, —$(CH_2)_j$OC(O)R$^3$, —$(CH_2)_j$NR$^4$R$^5$, —$(CH_2)_j$C(O)NR$^4$R$^5$, —$(CH_2)_j$OC(O)NR$^4$R$^5$, —$(CH_2)_j$NR$^6$C(O)R$^3$, —$(CH_2)_j$NR$^6$C(O)OR$^3$, —$(CH_2)_j$NR$^6$C(O)NR$^4$R$^5$, —$(CH_2)_j$S(O)$_m$R$^7$, —$(CH_2)_j$S(O)$_2$NR$^4$R$^5$, —$(CH_2)_j$NR$^6$S(O)$_2$R$^7$, or —$(CH_2)_j$OP(O)(O)$_2$.

In another aspect, the disclosure provides a compound of Formula I, wherein $R^2$ is independently —$(CH_2)_j$OR$^3$, —$(CH_2)_j$OC(O)NR$^4$R$^5$, or —$(CH_2)_j$OP(O)(OR$^7$)$_2$.

In another aspect, the disclosure provides a compound of Formula I, wherein $R^3$ is hydrogen; $R^4$ and $R^5$ are $(C_1-C_6)$alkyl; and $R^7$ is $(C_1-C_6)$alkyl, or phenyl.

In another aspect, the disclosure provides a compound of Formula I, wherein $R^2$ is independently —$(CH_2)_j$OR$^3$; $R^3$ is arylalkyl; and $R^8$ is halogen.

In another aspect, the disclosure provides a compound of Formula I, having formula:

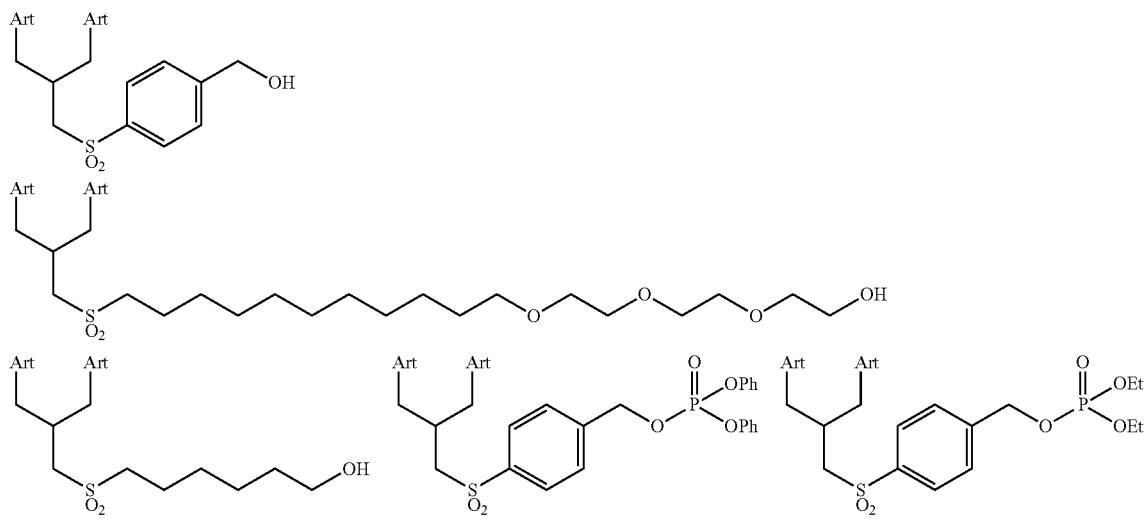

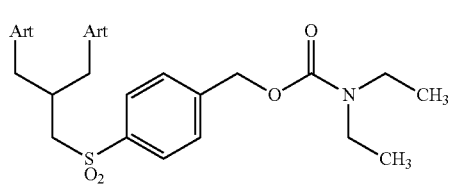
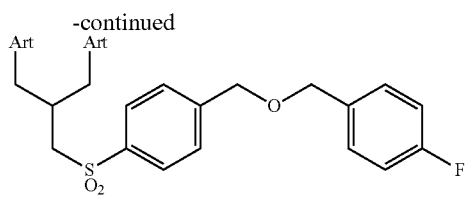

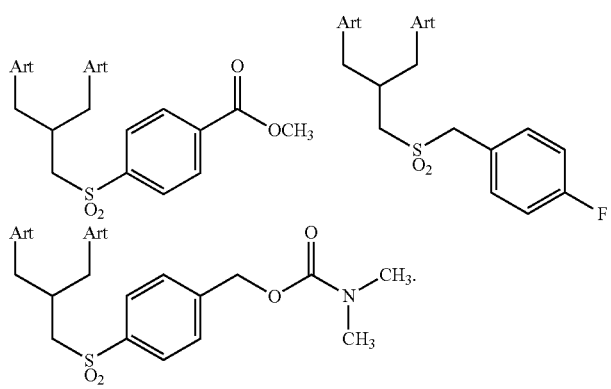

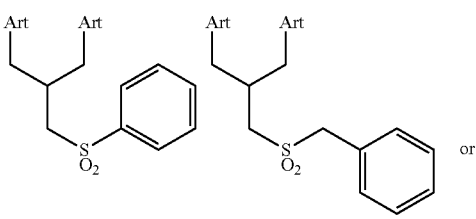

In another aspect, the disclosure provides methods for preparing the compound of Formula I, comprising the steps of:

a) reacting the compound of Formula II with $R^1SH$ and base to provide the sulfide compound of Formula I; and b) optionally treating the sulfide compound of Formula I with an oxidizing agent to provide the sulfoxide and/or sulfone compound of Formula I:

wherein X is a leaving group.

In another aspect, the disclosure provides methods for preparing the compound of Formula I, comprising the steps of:

a) reacting the compound of Formula II with $R^1SH$ and base to provide the sulfide compound of Formula I; and b) optionally treating the sulfide compound of Formula I with an oxidizing agent to provide the sulfoxide and/or sulfone compound of Formula I, wherein X is halogen, mesylate, tosylate or triflate; and the base is 1,8-diazabicyclo[5.4.0]undec-7-ene (DBU), sodium hydride, or pyridine.

In another aspect, the disclosure provides the compound of Formula I, prepared by any of the methods disclosed herein.

In another aspect, the disclosure provides pharmaceutical compositions comprising a pharmaceutically acceptable excipient and a compound of Formula I.

In another aspect, the disclosure provides methods for treating cancer in a subject in need of such treatment, by administering to the subject a therapeutically effective amount of a compound of Formula I.

In another aspect, the disclosure provides methods for treating cancer in a subject in need of such treatment, by administering to the subject a therapeutically effective amount of a compound of Formula I, wherein the cancer is leukemia, non-small cell lung cancer, colon cancer, central nervous system cancer, melanoma cancer, ovarian cancer, renal cancer, prostate cancer, and breast cancer.

In another aspect, the disclosure provides methods for treating malaria in a subject in need of such treatment, by administering to the subject a therapeutically effective amount of a compound of Formula I.

In Vivo Antimalarial Activity

The disclosed compounds of Formula I may provide an unexpectedly higher and longer lasting oral in vivo antimalarial activity in mouse model studies than the compounds in the prior art. For example, complete (or substantial, e.g. 3 of 5 mice) cure (survival with no detectable parasitemia at 30 days post-infection) of malaria-infected mice with a single 54 mg/kg dose may be achieved with some of the following new dimers:

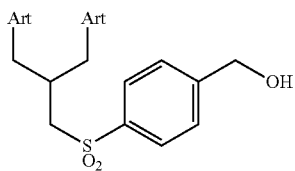
6

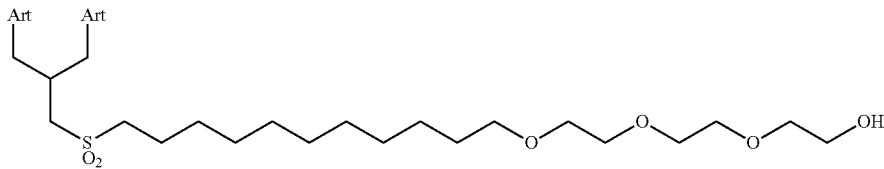
7

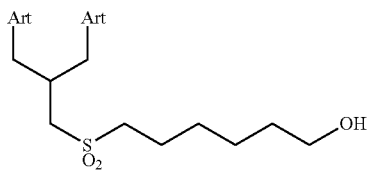
8

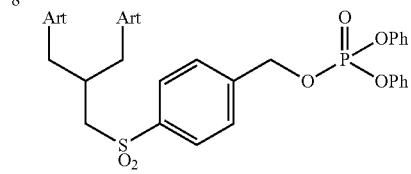
9

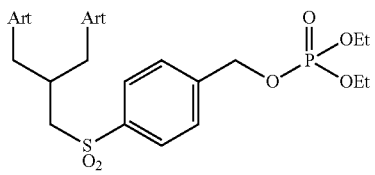
10

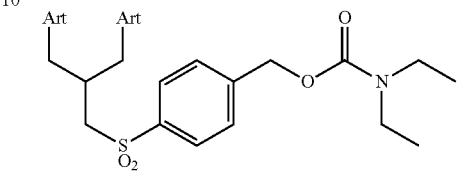
11

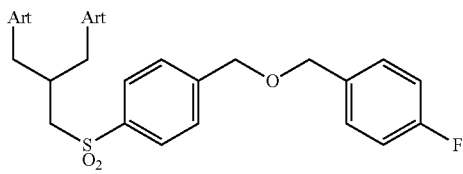
12

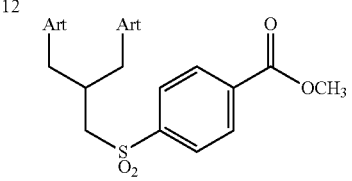
13

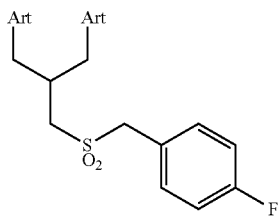
14

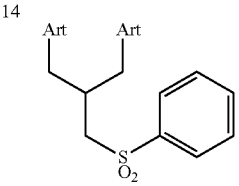
15

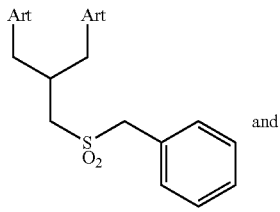
and
16

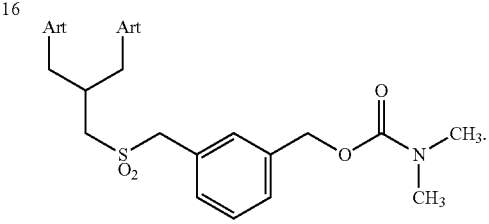
17

Determination of In Vitro Antimalarial Activity

To determine the antimalarial effect of the disclosed trioxane sulfur dimer compounds of Formula I, screening assays may be performed against chloroquine-sensitive *P. falciparum* (NF54). Using the methods described below, the $IC_{50}$ values of these compounds may be determined.

Antimalarial activity may be determined by measuring the incorporation of [$^3$H]hypoxanthine by the methods of Desjardins and Milhous with the following modifications, see Desjardins, R. E.; Canfield, C. J.; Haynes, J. D.; Chulay, J. D., Antimicrob. Agents Chemother., 16:710 (1979); Milhous, W. K.; Weatherly, N. F.; Bowdre, J. H.; Desjardins, R., Antimicrob. Agents Chemother., 27:525 (1985). Chloroquine-sensitive *P. falciparum* (NF54 strain) is maintained in a 2.4% suspension of type O$^+$ human erythrocytes (obtained weekly from a rotating pool of screened healthy volunteers) in RPMI 1640 (Gibco BRL #13200-076), supplemented with 25 mM N-2-hydroxyethylpiperazine-N'2-ethanesulfonic acid (HEPES; Calbiochem #391338), 27 mM NaHCO$_3$ (Gibco BRL #11810-025), and 10% heat-inactivated human type O$^+$ serum (Interstate Blood Bank, Inc.), under 3% O$_2$, 4% CO$_2$, and 93% N$_2$. Parasitemia is maintained at 0.05-3% and doubling time at approximately 15 hours by twice weekly change of medium and replenishment with fresh erythrocytes.

Stock solutions (approximately 2.5 mg/mL of HPLC-purified or recrystallized test compound) are prepared in dimethyl sulfoxide (DMSO; Sigma-Aldrich #27,043-1). DMSO solutions are diluted 500-fold in medium, serially diluted in 0.2% DMSO in medium (to maintain constant solvent concentration), then 100 μL aliquots are pipetted into microtiter plate wells (Costar3595). Provisional $EC_{50}$ values are obtained in a survey of seven 5-fold dilutions yielding final concentrations (in triplicate) of 0.16-2500 ng/mL. These assays may be later expanded to include ten concentrations (in quadruplicate) of approximately 1.8-fold dilutions which flank the provisional $EC_{50}$. Plates may include at least 8 wells of no drug controls (4 with and 4 without DMSO) and 4 wells of uninfected erythrocytes. Parasite culture (0.25% parasitemia in 2.4% hematocrit; 100 μL per well) may be added and the plate incubated for 48 hours prior to the addition of 25 μL [$^3$H]hypoxanthine (14.1 Ci/mmol, 1 mCi/mL in 70% ethanol, New England Nuclear NET-177, diluted to 25 μCi/mL with medium) and subsequent 20 hour incubation. Cells may be harvested (Brandel MB-48R) onto GF-C glass filters (Brandel), and the filters washed five times with 3 mL water per sample spot, dried under a heat lamp, and counted (Beckman Model LS-6500) in scintillation cocktail (ICN Cytoscint).

Decays per minute (dpm) values may be downloaded and analyzed (Power Macintosh 7200/90; Microsoft Excel 5.0), to yield the mean and standard deviation at each drug concentration. Dose-response curves may be fit to the experimental data (Delta Point DeltaGraph 3.5.3) by means of the Marquardt algorithm, which may be solved for the drug concentration that kills 50% of parasites, and analyzed for goodness of fit (R.sup.2 value).

In sharp contrast to the potency of the natural trioxane artemisinin ($IC_{50}$=7.7 nm), the trioxane sulfur dimer compounds of Formula I may have substantially enhanced potencies. In addition, further derivitization of these potent antimalarial drugs may produce a number of analogs having antimalarial active in the sub-nanomolar concentrations.

Determination of Antitumor Activities

Growth Inhibition

To determine the growth inhibition (GI) and cytotoxicity of the disclosed trioxane dimer sulfur compounds of Formula I, screening assays may be performed by the National Cancer Institute using a 60 cell line panel.

The screening assay may be performed on 96-well microtitre plates. Relatively high initial inoculation densities may be used, in order to permit measurement of "time-zero" values and to enhance the screen's ability to detect and provide some differentiation between growth inhibition and cytotoxic response parameters. The specific inoculation densities (which range from 5,000 to 40,000 cells/well) used for each cell line are those which, for the respective line, may be determined to give an optical density signal for both the "time-zero" value (at 24 hours) and the "no-drug" control (at 72 hours) above the noise level and within the linear range of the end-point assay (which measures cellular protein). The inoculated microtitre plates are pre-incubated for 24 hours at 37° C. prior to drug additions. The five drug dilutions tested routinely range from $10^{-4}$ to $10^{-8}$ molar. Higher or lower concentration ranges may be selected on a non-routine basis if appropriate solubility and/or prior biological information or other screening data so dictate. Duplicate wells may be prepared for all concentrations, (concentration is often denoted by placing brackets around a number); "time-zero" and "no drug" controls are also provided for each test. The minimum amount of compound required for a one-time evaluation in the routine screen can be calculated from the knowledge that each test requires a total of approximately 40 ml (0.04 liter) of cell culture medium containing the highest desired drug concentration. Thus, the amount (grams) of sample required (assuming an upper test concentration limit of $10^{-4}$ M) is: molecular weight of compound×$10^{-4}$×0.04. After a 48 hour incubation (37° C.) with the test compound, the cells are fixed in situ to the bottoms of the microtitre wells by addition of 50 μl of either 50% trichloroacetic acid (for adherent cell lines) or 80% trichloroacetic acid (for settled cell suspension lines), followed by incubation for 60 minutes at 4° C. The cellular protein in each well is assayed using a sulforhodamine B (SRB) stain procedure. Briefly, after discarding the supernatants, the microtitre plates are washed 5 times with deionized water and air-dried. One hundred microliters of SRB solution (0.4% w/v in 1% acetic acid) is added to each microtitre well and incubated for 10 minutes at room temperature. Unbound SRB is removed by washing 5 times with 1% acetic acid. The plates are air-dried, the bound stain is solubilized with Tris buffer, and the optical densities read at 515 nm. SRB is a bright pink anionic dye which, in dilute acetic acid, binds electrostatically to the basic amino acids of TCA-fixed cells. Cryopreserved master stocks of all the lines are maintained, and cultures used for screening may be replaced from the master stock after no more than twenty passages in the screening laboratory. The cell line panel consists of 60 lines, organized into nine, disease-related subpanels including leukemia, non-small-cell lung cancer, colon, CNS, melanoma, ovarian, renal, prostate and breast cancers.

The response parameters $GI_{50}$ and $LC_{50}$ are interpolated values representing the concentrations at which the percentage growth (PG) is +50 and −50, respectively:

$GI_{50}$ is the concentration for which the PG=+50. At this value the increase from time $t_0$, in the number or mass of cells in the test well is only 50% as much as the corresponding increase in the control well during this period of the experiment. A drug effect of this intensity is interpreted as primary growth inhibition.

TGI is the concentration for which PG=0. At this value the number or mass of cells in the well at the end of the experiment equals the number or mass of cells in the well at time $t_0$. A drug effect of this intensity is regarded as cytostasis.

Acute Toxicity Study of Three Anti-Malarial Compounds in Male CD-1 Mice

The purpose of this study is to determine the relative toxicity of the structurally similar anti-malarial compounds and sodium artesunate following a single intraperitoneal (ip) injection. This study may be performed in compliance with the U.S. FDA "Good Laboratory Practice for Nonclinical Laboratory Studies" (GLP) as described in 21 CFR Part 58; however, documentation of all procedures and quality control checking of data was performed as for GLP studies.

Materials and Methods

A. Test Article and Dose Preparation

The disclosed compounds of Formula I and sodium artesunate (Mepha Ltd., Lot No. 1), may be provided by NIAID via McKesson BioServices HBOC (Rockville, Md.). Each compound may be dissolved in DMSO (Mallinkrodt Lot No. V18H15) to achieve a concentration of 200 mg/ml, and then 3 parts sesame oil (Spectrum Lot No. M10656) was added to make a working concentration of 50 mg/ml for dose administration. Stability, strength, and uniformity of the test articles in the dose formulations are not determined for this study.

B. Test System

CD1 male mice purchased from Charles River Laboratories (Wilmington, Mass.) may be used in the study. Mice may be quarantined for 3 days prior to initiation of the study. General procedures for animal care and housing were in accordance with the National Research Council (NRC) Guide for the Care and Use of Laboratory Animals (1996) and the animal welfare standards incorporated in 9 CFR Part 3, 1991. Mice may be approximately 6 weeks old and weighed 25.2-31.2 g at study initiation. They may be individually housed under a 12 hr light-dark cycle, with a temperature range of 68-72° F. and 33-67% humidity. Purina Certified Rodent Chow #5002 and purified tap water were available ad libitum.

C. Experimental Design and Data Collection

Mice may be weighed and randomized into treatment groups on the day prior to the first dose administration. Due to limitations in the amount of available test materials, fewer mice in 1000 mg/kg groups are treated than specified in the protocol. Mice may be administered either a compound of Formula I or sodium artesunate once ip at does levels at 125, 250, 500, or 1000 mg/kg. Control animals may be administered a vehicle solution (25% DMSO and 75% sesame oil) at a volume of 20 ml/kg. Surviving animals may be sacrificed on Day 8 and blood may be collected for clinical pathology evaluations.

Clinical signs may be observed daily, including evaluation of the injection site 1 to 2 hr. after treatment on Day 1 and once daily on Days 2-8. Mortality and morbidity may be checked twice daily on weekdays and once daily on the weekend. Animals may be weighed daily and prior to necropsy.

In conclusion, the disclosed trioxane dimer sulfur compounds of Formula I, which are easily prepared on a gram scale and are thermally stable, can be prepared without destroying the critical pharmacophore peroxide bond. Each of the new trioxane dimers may be more antimalarially potent in vitro than the natural trioxane artemisinin (I), and may be inhibitory but not cytotoxic toward several human cancer cell lines. These semi-synthetic new chemical entities, therefore, deserve further preclinical evaluation as potential drug candidates for chemotherapy of malaria and cancer. These trioxane sulfur dimers may be more efficacious (when administered both orally and i.v.) and may be less toxic (when administered intraperitoneally to mice as a single dose) than clinically-used sodium artesunate, thereby giving them a better antimalarial therapeutic index than sodium artesunate.

Pharmaceutical Compositions and Administration

In another aspect, the present disclosure provides a pharmaceutical composition including trioxane dimer sulfur compounds of Formula I in admixture with a pharmaceutically acceptable excipient. One of skill in the art will recognize that the pharmaceutical compositions include the pharmaceutically acceptable salts of the compounds described above.

In therapeutic and/or diagnostic applications, the compounds of the disclosure can be formulated for a variety of modes of administration, including systemic and topical or localized administration. Techniques and formulations generally may be found in Remington: The Science and Practice of Pharmacy (20$^{th}$ ed.) Lippincott, Williams & Wilkins (2000).

The compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20$^{th}$ ed.) Lippincott, Williams & Wilkins (2000). Pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington: The Science and Practice of Pharmacy (20$^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intrasynovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g. patient) to be treated.

For nasal or inhalation delivery, the agents of the disclosure may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Depending upon the particular condition, or disease state, to be treated or prevented, additional therapeutic agents, which are normally administered to treat or prevent that condition, may be administered together with the inhibitors of this disclosure. For example, chemotherapeutic agents or other anti-proliferative agents may be combined with the inhibitors of this disclosure to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Other examples of agents in which the disclosed trioxane sulfur dimer compounds may also be combined with include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

These additional agents may be administered separately, as part of a multiple dosage regimen, from the inhibitor-containing composition. Alternatively, these agents may be part of a single dosage form, mixed together with the inhibitor in a single composition.

The present disclosure is not to be limited in scope by the exemplified embodiments, which are intended as single illustrations. Indeed, various modifications of the disclosure in addition to those described herein will become apparent to those having skill in the art from the foregoing description. Such modifications are intended to fall within the scope of the disclosure. Moreover, any one or more features of any embodiment of the disclosure may be combined with any one or more other features of any other embodiment of the disclosure, without departing from the scope of the claims. References cited throughout this application are examples of the level of skill in the art and are hereby incorporated by reference herein in their entirety for all purposes, whether previously specifically incorporated or not.

The disclosure is further illustrated by the following non-limited examples. All scientific and technical terms have the meanings as understood by one with ordinary skill in the art. The specific examples which follow illustrate the synthesis of representative compounds of the disclosure and are not to be construed as limiting the disclosure in sphere or scope. The methods may be adapted to variation in order to produce compounds embraced by the disclosure but not specifically disclosed. Further, variations of the methods to produce the same compounds in somewhat different fashion will be evident to one skilled in the art. The synthetic descriptions and specific examples that follow are only intended for the purposes of illustration, and are not to be construed as limiting in any manner to make compounds of the disclosure by other methods. All publications, patents, and patent applications cited herein are hereby incorporated by reference in their entirety for all purposes.

EXAMPLES

The following examples are offered to illustrate, but not to limit the claims.

All air- and moisture-sensitive reactions were performed under argon in oven-dried or flame-dried glassware. Tetrahydrofuran (THF) and diethyl ether (ether) were distilled from sodium-benzophenone ketyl and dichloromethane was distilled from calcium hydride under nitrogen. Dimethyl sulfoxide and hexamethylphosphoric triamide were distilled from calcium hydride over 4 Å molecular sieves under reduced pressure. Solvents and solutions for air- and moisture-sensitive reactions were transferred via syringe or cannula. All experiments were monitored by thin layer chromatography (tlc) performed on EM Science precoated silica gel 60 F-254 glass supported plates with 0.25 mm thickness. Flash chromatography was performed with EMD silica gel (40-63 µm). Yields are not optimized. Purity of final products was confirmed by two diverse high performance liquid chromatography (HPLC) trace analyses. HPLC was performed with a Rainin HPLX gradient system equipped with two 25 mL/min preparative pump heads using Phenomenex 10 mm×250 mm (semi-preparative) column packed with 60 Å silica gel. Melting points were measured using a MeI-Temp metal-block apparatus and are uncorrected. Infrared (IR) spectra were recorded on a Bruker Vector 33 FT-IR spectrophotometer or a Perkin Elmer 1600 FT-IR spectrometer. Nuclear Magnetic Resonance (NMR) spectra were recorded on a Bruker Avance 400 MHz FT-NMR spectrometers (400 MHz for $^1$H, 100 MHz for $^{13}$C) or Bruker Avance 300 MHz FT-NMR spectrometer (300 MHz for $^1$H, 282 MHz for $^{19}$F, 75 MHz for $^{13}$C). Residual signals [$^1$H: 7.26 ppm, $^{13}$C: 77.0 ppm for CDCl$_3$; $^1$H, 2.50 ppm, $^{13}$C: 39.52 ppm for (CD$_3$)$_2$SO; $^1$H, 3.31 ppm, $^{13}$C: 49.0 ppm for CD$_3$OD; $^1$H, 2.05 ppm, $^{13}$C: 29.84 ppm for (CD$_3$)$_2$CO] were used as internal standards. The following abbreviations are used in the experimental section for the description of $^1$H NMR spectra: singlet (s), doublet (d), triplet (t), quartet (q), multiplet (m), broad singlet (bs), doublet of doublets (dd), doublet of triplets (dt), and doublet of quartets (dq). Low and high resolution mass spectra (LRMS and HRMS) were obtained on a VG70S magnetic sector mass spectrometer at Johns Hopkins University with fast atom bombardment (FAB) ionization or a 3-Tesla Finnigan FTMS-2000 Fourier Transform mass spectrometer at Ohio State University with electrospray ionization (ESI). Combustion analyses were conducted by Atlantic Microlab (Norcross, Ga.). Reagents were purchased from Aldrich Chemical Company unless otherwise noted. Various methods of purifying the products of the present disclosure known and understood by those skilled in the art and the purification methods presented are solely listed by way of example and are not intended to be limiting.

Example 1

Synthesis of ASR-isobu-SO$_2$-Ph-4-CH$_2$OH (6)

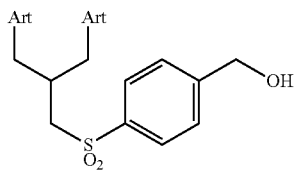

Bis-trioxane bromide (39 mg, 0.058 mmol) was dissolved in acetonitrile (3 mL) under argon at room temperature. To the solution was added 4-hydroxymethyl thiophenol (16 mg, 0.116 mmol) and NaH (3.0 mg, 0.116 mmol) consecutively and the reaction was stirred at room temperature overnight. The reaction was quenched with sat. aq. sodium bicarbonate (2 mL) and extracted with EtOAc (2 mL). The organic layer was then washed with ice cold distilled water (2×2 mL) and brine (2 mL). The organic layer was dried with MgSO$_4$, filtered, and concentrated in vacuo. The crude product was dissolved in dichloromethane (3 mL). mCPBA (10 mg, 0.057 mmol) was added at room temperature and stirred for 2 h. The reaction was quenched with saturated aqueous sodium bisulfite (2 mL) and the organic layer was extracted with sat. aq. sodium bicarbonate (2 mL). The crude product was purified by flash silica gel column chromatography (20→30% EtOAc/hexanes) to yield ASR-isobu-SO$_2$-Ph-4-CH$_2$OH 6 (25 mg, 0.033 mmol, 57%) as an amorphous white solid. mp=109-112° C.; [α]$_D^{21.3}$+55° (c=0.55, CHCl$_3$); IR (thin film) 3511, 2948, 2848, 1454, 1408, 1306, 1197, 1142, 1094, 1051, 1008, 936, 880, 837, 763 cm$^{-1}$; $^1$H NMR (400 MHz, CDCl$_3$) δ 7.97-7.95 (d, 2H), 7.49-7.47 (d, 2H), 5.44 (s, 1H), 5.32 (s, 1H), 4.76 (s, 2H), 4.11-4.06 (m, 1H), 3.63-3.58 (dd, J$_1$=14 Hz, J$_2$=8.0 Hz, 1H), 3.34-3.29 (dd, J$_1$=14 Hz, J$_2$=8.0 Hz, 1H), 2.71-2.64 (m, 1H), 2.57-2.49 (m, 1H), 2.51-2.44 (m, 1H), 2.37-2.25 (m, 2H), 2.20-1.16 (m, 29H, including singlets at 1.42 and 1.34 for 3H each), 0.95-0.91 (m, 8H), 0.83-0.80 (m, 7H); $^{13}$C NMR (100 MHz, CDCl$_3$) δ 146.8, 139.2, 128.3, 127.0, 103.4, 102.9, 89.5, 88.8, 81.3, 81.2, 73.9, 71.0, 62.2, 60.4, 58.9, 52.5, 52.1, 44.6, 44.1, 37.4, 36.6, 36.6, 34.5, 34.4, 31.2, 31.1, 30.7, 30.4, 26.2, 26.1, 24.8, 24.8, 21.1, 20.3, 20.1, 14.2, 13.3, 12.7.

Example 2

Synthesis of ASR-isobu-SO$_2$-diglyme-OH (7)

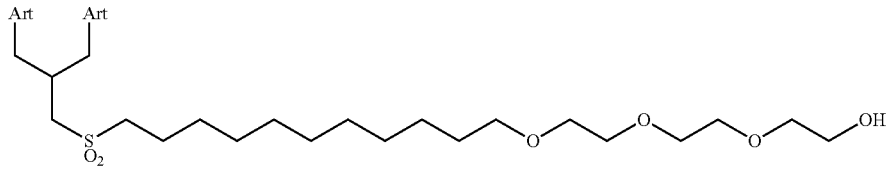

Bis-trioxane bromide 3 (10 mg, 0.015 mmol) was dissolved in 70% ethanol (EtOH) in water (1 mL) under argon at room temperature. To the solution was added triethylene glycol mono-11-mercaptoundecyl ether (12 μL, 0.030 mmol) and 1,8-diazabicyclo[5.4.0]-undec-7-ene (DBU) (4.5 μL, 0.030 mmol) consecutively, and the reaction was heated at reflux for 1.5 h. The reaction was quenched with saturated aqueous sodium bicarbonate (2 mL) and extracted with dichloromethane (2×2 mL). The organic layer was dried with MgSO$_4$, filtered, and concentrated in vacuo. The crude product was dissolved in dichloromethane (1 mL). mCPBA (10 mg, 0.030 mmol) was added at room temperature and stirred for 2 h. The reaction was quenched with saturated aqueous sodium bisulfite (2 mL) and the organic layer was washed with saturated aqueous sodium bicarbonate (2 mL). The crude product was purified by flash silica gel column chromatography (100% EtOAc) to yield ASR-isobu-SO$_2$-diglyme-OH 7 (4.5 mg, 0.005 mmol, 32%) as an amorphous white solid. $^1$H NMR (400 MHz, CDCl$_3$) δ 5.41 (s, 1H), 5.34 (s, 1H), 4.47-4.43 (m, 1H), 4.22-4.18 (m, 1H), 3.74-3.71 (m, 3H), 3.69-3.57 (m, 13H), 3.47-3.43 (t, J=6.8 Hz, 3H), 3.14-3.09 (m, 1H), 3.08-3.04 (m, 2H), 2.74-2.69 (m, 1H), 2.60-2.55 (m, 2H), 2.37-2.21 (m, 4H), 2.04-1.20 (m, 41H including singlets for 3H each at 1.40 and 1.27), 0.97-0.94 (m, 8H), 0.87-0.85 (m, 6H); $^{13}$C NMR (100 MHz, CDCl$_3$) δ 102.9, 102.7, 89.6, 86.7, 81.3, 74.8, 73.8, 71.6, 70.6, 70.5, 70.4, 70.0, 61.8, 40.6, 37.5, 37.3, 36.7, 34.6, 31.2, 30.6, 30.3, 29.6, 29:5, 29.5, 29.4, 29.1, 28.6, 26.1, 26.1, 24.8, 24.7, 21.7, 20.3, 20.1, 12.7.

Example 3

Synthesis of ASR-isobu-SO$_2$—(CH$_2$)$_6$OH (8)

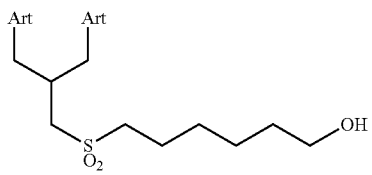

Bis-trioxane bromide 3 (20 mg, 0.030 mmol) was dissolved in anhydrous acetonitrile (2 mL) under argon at room temperature. To the solution was added 6-mercapto-1-hexanol (9 µL, 0.066 mmol) and sodium hydride (NaH) (2.0 mg, 0.066 mmol) consecutively and the reaction was stirred at room temperature for 2 h. The reaction was quenched with saturated aqueous sodium bicarbonate (2 mL) and extracted with dichloromethane (2×2 mL). The organic layer was dried with MgSO$_4$, filtered, and concentrated in vacuo. The crude product was dissolved in freshly made dimethyldioxirane solution in acetone (DMDO, 2 mL) at 0° C. and stirred for 1 h. The reaction was concentrated the crude product was purified by flash silica gel column chromatography (50% EtOAc/hexanes) to yield ASR-isobu-SO$_2$—(CH$_2$)$_6$OH 8 (12 mg, 0.015 mmol, 51%) as an amorphous white solid. $^1$H NMR (400 MHz, CDCl$_3$) δ 5.41 (s, 1H), 5.34 (s, 1H), 4.46-4.42 (m, 1H), 4.20-4.16 (m, 1H), 3.65-3.62 (t, J=6.4 Hz, 2H), 3.49-3.42 (dd, J$_1$=14.2 Hz, J$_2$=7.2 Hz, 1H), 3.10-3.05 (m, 3H), 2.74-2.69 (m, 1H), 2.60-2.54 (m, 2H), 2.35-2.27 (m, 3H), 2.03-1.21 (m, 34H including singlets for 3H each at 1.40 and 1.25), 0.96-0.94 (m, 8H), 0.87-0.85 (m, 8H);); $^{13}$C NMR (100 MHz, CDCl$_3$) δ 103.3, 102.9, 89.7, 88.8, 81.3, 81.2, 73.7, 70.3, 62.7, 55.7, 53.0, 52.6, 52.1, 44.5, 44.1, 37.5, 37.3, 36.7, 36.6, 34.6, 34.4, 32.3, 31.9, 31.6, 30.6, 30.3, 29.8, 29.7, 28.2, 26.2, 26.1, 25.1, 24.8, 24.8, 24.7, 24.7, 21.6, 20.3, 20.1, 13.2, 12.6.

Example 4

Synthesis of ASR-isobu-SO$_2$-Ph-CH$_2$OP(O)(OPh)$_2$ (9)

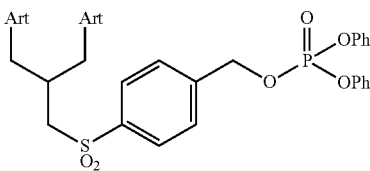

ASR-isobu-SO$_2$-Ph-CH$_2$OH 6 (10 mg, 0.013 mmol) was dissolved in anhydrous dichloromethane (1 mL) under argon at room temperature. To the solution was added diphenyl chlorophosphate (13 µL, 0.065 mmol) and pyridine (5 µL, 0.065 mmol) consecutively and the reaction was stirred at room temperature for 18 h. The reaction was quenched with saturated aqueous sodium bicarbonate (2 mL) and extracted with dichloromethane (2×2 mL). The organic layer was dried with MgSO$_4$, filtered, and concentrated in vacuo. The crude product was purified by flash silica gel column chromatography (40% EtOAc/hexanes) to yield ASR-isobu-SO$_2$-Ph-CH$_2$OP(O)(OPh)$_2$9 (8 mg, 0.008 mmol, 62%) as an amorphous white solid. $^1$H NMR (400 MHz, CDCl$_3$) δ 8.02-8.00 (d, J=8.4 Hz, 2H), 7.47-7.45 (d, J=8.4 Hz, 2H), 7.35-7.31 (t, J=8.4 Hz, 4H), 7.22-7.17 (t, J=8.4 Hz, 6H), 5.48 (s, 1H), 5.35 (s, 1H), 5.32 (s, 1H), 5.30 (s, 1H), 4.48-4.43 (m, 1H), 4.16-4.12 (m, 1H), 3.66-3.61 (dd, J=14.4 Hz, 1H), 3.38-3.33 (dd, J=14.4 Hz, 1H), 2.71-2.65 (m, 1H), 2.58-2.53 (m, 2H), 2.37-2.27 (m, 2H), 2.24-2.15 (m, 1H), 2.07-1.97 (m, 2H), 1.95-1.85 (m, 2H), 1.82-1.18 (m, 23H including singlets for 3H each at 1.42 and 1.34), 0.96-0.0.94 (m, 8H), 0.85-0.82 (m, 6H); $^{13}$C NMR (100 MHz, CDCl$_3$) δ 140.7, 129.9, 128.6, 127.9, 125.6, 120.1, 120.0, 103.3, 103.9, 89.5, 88.9, 81.3, 81.2, 74.0, 70.8, 69.2, 67.0, 64.9, 52.5, 52.1, 44.6, 44.1, 37.5, 37.4, 36.7, 34.6, 34.4, 31.3, 31.2, 30.4, 26.3, 26.1, 24.8, 20.3, 20.1, 13.3, 12.7.

Example 5

Synthesis of ASR-isobu-SO$_2$-Ph-CH$_2$OP(O)(OEt)$_2$ (10)

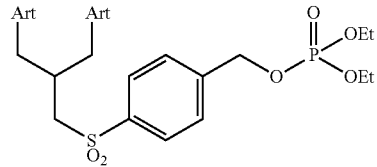

ASR-isobu-SO$_2$-Ph-CH$_2$OH 6 (20 mg, 0.026 mmol) was dissolved in anhydrous dichloromethane (2 mL) under argon at room temperature. To the solution was added diethyl chlorophosphate (19 µL, 0.13 mmol) and pyridine (11 µL, 0.13 mmol) consecutively and the reaction was stirred at room temperature for 18 h. The reaction was quenched with saturated aqueous sodium bicarbonate (2 mL) and extracted with dichloromethane (2×2 mL). The organic layer was dried with MgSO$_4$, filtered, and concentrated in vacuo. The crude product was purified by flash silica gel column chromatography (50% EtOAc/hexanes) to yield ASR-isobu-SO$_2$-Ph-CH$_2$OP(O)(OEt)$_2$ 10 (8.2 mg, 0.009 mmol, 37%) as an amorphous white solid. $^1$H NMR (400 MHz, CDCl$_3$) δ 8.06-8.03 (d, J=8.0 Hz, 2H), 7.54-7.52 (d, J=8.0 Hz, 2H), 5.49 (s, 1H), 5.35 (s, 1H), 5.14-5.12 (d, J=8.0 Hz, 2H), 4.48-4.43 (m, 1H), 4.16-4.08 (m, 5H), 3.66-3.61 (dd, J=14 Hz, 1H), 3.39-3.34 (dd, J=14 Hz, 1H), 2.70-2.66 (m, 1H), 2.58-2.53 (m, 2H), 2.38-2.28 (m, 2H), 2.23-2.16 (m, 1H), 2.06-2.00 (m, 2H), 1.93-1.90 (m, 2H), 1.79-1.21 (m, 29H including singlets for 3H each at 1.44 and 1.35), 0.96-0.95 (m, 8H), 0.85-0.82 (m, 6H); $^{13}$C NMR (100 MHz, CDCl$_3$) δ 140.5, 138.0, 128.6, 127.7, 103.3, 102.9, 89.6, 88.9, 81.3, 81.2, 74.0, 70.9, 67.8, 67.7, 64.1, 64.1, 58.8, 57.2, 57.1, 52.6, 52.2, 44.6, 44.1, 37.5, 37.4, 36.7, 36.7, 34.4, 31.3, 30.7, 30.4, 29.7, 26.2, 26.1, 24.8, 24.8, 20.2, 20.1, 16.2, 16.1, 14.2, 13.2, 12.6.

Example 6

Synthesis of ASR-isobu-SO$_2$-Ph-CH$_2$OC(O)NEt$_2$ (11)

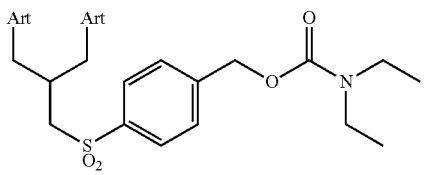

ASR-isobu-SO$_2$-Ph-CH$_2$OH 6 (10 mg, 0.013 mmol) was dissolved in anhydrous dichloromethane (1 mL) under argon at room temperature. To the solution was added diethylcarbamyl chloride (4 μL, 0.026 mmol) and NaH (0.62 mg, 0.026 mmol) consecutively and the reaction was stirred at room temperature for 2 h. The reaction was quenched with saturated aqueous sodium bicarbonate (2 mL) and extracted with dichloromethane (2×2 mL). The organic layer was dried with MgSO$_4$, filtered, and concentrated in vacuo. The crude product was purified by flash silica gel column chromatography (30% EtOAc/hexanes) to yield ASR-isobu-SO$_2$-Ph-CH$_2$OC(O)NEt$_2$ 11 (7.5 mg, 0.009 mmol, 68%) as an amorphous white solid. $^1$H NMR (400 MHz, CDCl$_3$) δ 8.03-8.01 (d, J=8 Hz, 2H), 7.49-7.47 (d, J=8 Hz, 2H), 5.48 (s, 1H), 5.34 (s, 1H), 5.19 (s, 2H), 4.47-4.44 (m, 1H), 4.16-4.12 (dd, J=4.4 Hz, 1H), 3.65-3.60 (dd, J=9.6 Hz, 1H), 3.38-3.33 (dd, J=9.6 Hz, 1H), 3.35-3.31 (m, 4H), 2.71-2.67 (m, 1H), 2.58-2.53 (m, 2H), 2.37-2.27 (m, 2H), 2.22-2.17 (m, 1H), 2.05-1.99 (m, 2H), 1.92-1.82 (m, 2H), 1.79-1.73 (m, 4H), 1.65-1.18 (m, 19H including singlets for 3H each at 1.43 and 1.34), 1.15-1.12 (t, J=6.8 Hz, 6H), 0.96-0.94 (d, J=6.4 Hz, 8H), 0.84-0.82 (d, J=7.2 Hz, 6H); $^{13}$C NMR (100 MHz, CDCl$_3$) δ 156.9, 142.9, 140.0, 128.4, 127.8, 103.3, 102.9, 89.5, 88.8, 81.3, 81.2, 73.9, 71.0, 65.7, 58.8, 52.6, 52.2, 44.6, 44.1, 37.4, 37.3, 36.7, 36.6, 34.6, 34.4, 31.3, 31.2, 31.2, 30.7, 30.4, 29.7, 26.2, 26.1, 24.8, 24.8, 24.7, 24.7, 20.2, 20.1, 13.2, 12.7.

Example 7

Synthesis of ASR-isobu-SO$_2$-Ph-CH$_2$OCH$_2$-Ph-4-F (12)

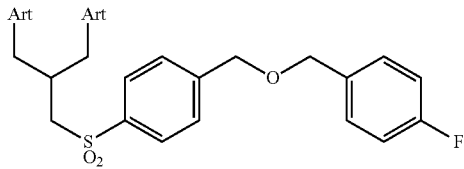

ASR-isobu-SO$_2$-Ph-CH$_2$OH 6 (10 mg, 0.013 mmol) was dissolved in anhydrous DMF (1 mL) under argon at room temperature. To the solution was added 4-fluorobenzyl bromide (3 μL, 0.026 mmol) and NaH (0.31 mg, 0.013 mmol) consecutively. The reaction went from colorless to foamy yellow. The reaction was stirred at room temperature for 2 h and quenched with saturated aqueous sodium bicarbonate (2 mL) and extracted with dichloromethane (2×2 mL). The organic layer was dried with MgSO$_4$, filtered, and concentrated in vacuo. The crude product was purified by flash silica gel column chromatography (30% EtOAc/hexanes) to yield ASR-isobu-SO$_2$-Ph-CH$_2$OCH$_2$-Ph-4-F 12 (10 mg, 0.012 mmol, 91%) as an amorphous white solid. $^1$H NMR (400 MHz, CDCl$_3$) δ 8.02-8.00 (d, J=8.0 Hz, 2H), 7.51-7.49 (d, J=8.0 Hz, 2H), 7.34-7.31 (m, 2H), 7.07-7.03 (m, 2H), 5.47 (s, 1H), 5.34 (s, 1H), 4.61 (s, 2H), 4.53 (s, 2H), 4.47-4.41 (m, 1H), 4.15-4.11 (m, 1H), 3.64-3.59 (dd, J=14.2 Hz, 1H), 3.38-3.33 (dd, J=14.2 Hz, 1H), 2.70-2.66 (m, 1H), 2.58-2.53 (m, 2H), 2.38-2.27 (m, 2H), 2.23-2.15 (m, 1H), 2.04-1.99 (m, 2H), 1.92-1.89 (m, 2H), 1.83-1.19 (m, 25H including singlets for 3H each at 1.46 and 1.37), 0.96-0.94 (m, 8H), 0.90-0.88 (m, 6H); $^{13}$C NMR (100 MHz, CDCl$_3$) δ 144.0, 139.7, 129.6, 129.5, 128.4, 127.7, 115.5, 115.3, 103.3, 102.9, 89.5, 88.8, 81.3, 81.2, 73.9, 71.8, 71.2, 58.9, 52.6, 52.2, 50.8, 44.6, 44.1, 37.4, 37.3, 36.7, 34.6, 34.4, 31.3, 30.7, 26.2, 26.1, 24.8, 24.8, 24.7, 24.7, 20.2, 20.1, 12.7.

Example 8

Synthesis of ASR-isobu-SO$_2$-Ph-4-COOMe (13)

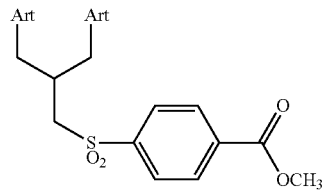

Bis-trioxane bromide (20 mg, 0.030 mmol) was dissolved in acetonitrile (2 mL) under argon at room temperature. To the solution was added 4-mercaptobenzoate (16 mg, 0.095 mmol, easily prepared by esterifying the commercially available acid) and NaH (2.0 mg, 0.095 mmol) consecutively and the reaction was stirred overnight. The reaction was quenched with sat. aq. sodium bicarbonate (2 mL) and diluted with EtOAc (2 mL). The organic layer was then washed with ice cold distilled water (2×2 mL) and brine (2 mL). The organic layer was dried with MgSO$_4$, filtered, and concentrated in vacuo. The crude product was dissolved in dichloromethane (3 mL). mCPBA (10 mg, 0.057 mmol) was added at room temperature and stirred for 2 h. The reaction was quenched with saturated aqueous sodium bisulfite (2 mL) and the organic layer was extracted with sat. aq. sodium bicarbonate (2 mL). The crude product was purified by flash silica gel column chromatography (0→20% EtOAc/hexanes) to yield ASR-isobu-SO$_2$-Ph-4-COOMe 13 (8.0 mg, 0.010 mmol, 33%) as an amorphous white solid. $[\alpha]_D^{22.2}$+85° (c=0.12, CHCl$_3$); IR (thin film) 2951, 2875, 1730, 1435, 1377, 1318, 1279, 1149, 1106, 1052, 1007, 715, 622 cm$^{-1}$; $^1$H NMR (400 MHz, CDCl$_3$) δ 8.21-8.09 (m, 4H), 5.46 (s, 1H), 5.34 (s, 1H), 4.49-4.45 (m, 1H), 4.15-4.11 (m, 1H), 3.96 (s, 3H), 3.75-3.70 (dd, J$_1$=14 Hz, J$_2$=8.0 Hz, 1H), 3.39-3.34 (dd, J$_1$=14 Hz, J$_2$=8.0 Hz, 1H), 2.73-2.66 (m, 1H), 2.60-2.51 (m, 1H), 2.39-2.26 (m, 2H), 2.22-2.13 (m, 1H), 2.09-1.98 (m, 2H), 1.95-1.18 (m, 27H including singlets at 1.45 and 1.35 for 3H each), 0.96-0.94 (m, 7), 0.84-0.82 (m, 6H); $^{13}$C NMR (100 MHz, CDCl$_3$) δ 165.7, 144.3, 134.4, 130.2, 128.3, 103.3, 102.9, 89.6, 88.8, 81.3, 81.2, 77.2, 74.1, 70.7, 58.4, 52.6, 52.5, 52.1, 44.5, 44.0, 37.5, 37.4, 36.6, 34.5, 34.4, 31.3, 31.3, 31.2, 30.7, 30.4, 26.3, 26.1, 24.8, 24.8, 24.7, 20.3, 20.1, 13.3, 12.7.

Example 9

Synthesis of ASR-isobu-SO$_2$—CH$_2$Ph-4-F (14)

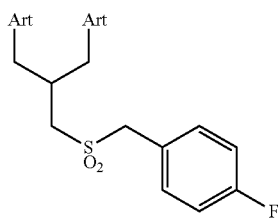

Bis-trioxane bromide 3 (10 mg, 0.015 mmol) was dissolved in DMF (0.5 mL) under argon. To the solution was added 4-fluorobenzyl mercaptan (2 µL, 0.018 mmol) and NaH (0.5 mg, 0.018 mmol) consecutively and the reaction was heated at 90° C. for 1 h. (Note: The reaction went from colorless to pink almost instantly upon heating. The pink color faded to a very light yellow over the course of the hour) The reaction was allowed to cool and was diluted with EtOAc (1 mL). The organic layer was then washed with ice cold distilled water (1 mL) and brine (1 mL). The organic layer was dried with MgSO$_4$, filtered, and concentrated in vacuo. The crude product was dissolved in CH$_2$Cl$_2$ (0.5 mL) and m-CPBA (4 mg, 0.020 mmol) was added. The reaction was stirred at room temperature for 5 h and then washed with saturated sodium bisulfite solution (1 mL) and saturated sodium bicarbonate solution (1 mL) sequentially. The organic layer was dried with MgSO$_4$, filtered, and concentrated in vacuo. The crude product was purified by flash silica gel column chromatography (0→20% EtOAc/hexanes) to yield ASR-isobu-SO$_2$—CH$_2$Ph-4-F 14 (6.5 mg, 0.010 mmol, 66%) as an amorphous white solid. $[\alpha]_D^{21.3}$+67.7° (c=0.35, CHCl$_3$); IR (thin film) 2938, 2876, 1509, 1456, 1377, 1309, 1226, 1118, 1099, 1056, 1007, 941, 878, 843 cm$^{-1}$; $^1$H NMR (400 MHz, CDCl$_3$) δ 7.48-7.44 (m, 2H), 7.08-7.04 (m, 2H), 5.48 (s, 1H), 5.31 (s, 1H), 4.40-4.38 (m, 1H), 4.35 (s, 2H), 4.15-4.13 (m, 1H), 3.54-3.50 (dd, J$_1$=14.3 Hz, J$_2$=10.1 Hz, 1H), 3.04-2.98 (dd, J$_1$=14.4 Hz, J$_2$=6.4 Hz, 1H), 2.78-2.72 (m, 1H), 2.65-2.56 (m, 2H), 2.39-2.28 (m, 311), 2.06-1.95 (m, 2H), 1.92-1.88 (m, 3H), 1.81-1.73 (m, 2H), 1.69-1.19 (m, 21H including singlets for 3H each at 1.42 and 1.37), 0.96-0.93 (dd, J$_1$=6.1 Hz, J$_2$=3.0 Hz, 7H), 0.86 (s, 3H), 0.84 (s, 3H); $^{13}$C NMR (100 MHz, CDCl$_3$) δ 133.0, 132.9, 123.7, 123.7, 115.9, 115.7, 103.4, 103.0, 89.5, 88.7, 81.3, 81.2, 77.2, 74.1, 70.5, 58.6, 54.6, 52.6, 52.1, 44.6, 44.2, 37.5, 37.2, 36.6, 34.6, 34.4, 31.5, 31.4, 30.4, 30.3, 30.1, 26.3, 26.1, 24.8, 24.8, 24.7, 24.7, 20.3, 20.1, 13.4, 12.8.

Example 10

Synthesis of ASR-isobu-SO$_2$-Ph (15)

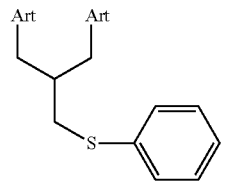

Bis-trioxane bromide (10 mg, 0.015 mmol) was dissolved in acetonitrile (1 mL) under argon at room temperature. To the solution was added thiophenol (2 µL, 0.018 mmol) and NaH (0.4 mg, 0.018 mmol) consecutively and the reaction was stirred at room temperature for 2 h. The reaction was extracted with EtOAc (2 mL). The organic layer was then washed with ice cold distilled water (2×2 mL) and brine (2 mL). The organic layer was dried with MgSO$_4$, filtered, and concentrated in vacuo. The crude product was purified by flash silica gel column chromatography (0→20% EtOAc/hexanes) to yield ASR-isobu-SO$_2$-Ph 15 (11 mg, 0.015 mmol, 100%) as an amorphous white solid. $^1$H NMR (400 MHz, CDCl$_3$) δ 7.42-7.38 (m, 2H), 7.25-7.21 (m, 2H), 7.14-7.09 (m, 1H), 5.32 (s, 1H), 5.29 (s, 1H), 4.37-4.32 (m, 1H), 4.22-4.17 (m, 1H), 3.32-3.16 (m, 2H), 2.73-2.67 (m, 1H), 2.59-2.52 (m, 1H), 2.37-2.19 (m, 3H), 2.04-1.19 (m, 28H including singlets at 1.39 and 1.35 for 3H each), 0.95-0.93 (m, 8H), 0.88-0.81 (m, 7H).

Example 11

Synthesis of ASR-isobu-SO$_2$—CH$_2$Ph (16)

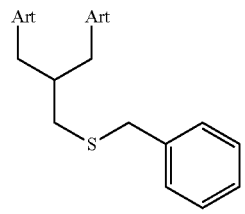

Bis-trioxane bromide 3 (40 mg, 0.060 mmol) was dissolved in DMF (2 mL) under argon. Benzyl mercaptan (8 µL, 0.072 mmol) and NaH (4 mg, 0.072 mmol) were added consecutively and the reaction was heated at 90° C. for 1 h. (Note: The reaction went from colorless to pink almost instantly upon heating. The pink color faded to a very light pink over the course of the hour) The reaction was allowed to cool and was diluted with EtOAc (2 mL). The organic layer was then washed with ice cold distilled water (2 mL) and brine (2 mL). The organic layer was dried with MgSO$_4$, filtered, and concentrated in vacuo. The crude product was dissolved in CH$_2$Cl$_2$ (2 mL) and m-CPBA (8 mg, 0.048 mmol) was added. The reaction was stirred at room temperature for 2 h and then washed with saturated sodium bisulfite solution (2 mL) and saturated sodium bicarbonate solution (2 mL) sequentially. The organic layer was dried with MgSO$_4$, filtered, and concentrated in vacuo. The crude product was purified by flash silica gel column chromatography (0→20% EtOAc/hexanes) to yield ASR-isobu-SO$_2$—CH$_2$Ph 16 (16 mg, 0.020 mmol, 87%) as an amorphous white solid. $[\alpha]_D^{21.5}$ +74.8° (c=0.30, CHCl$_3$); IR (thin film) 2924, 2875, 1455, 1377, 1308, 1188, 1119, 1100, 1056, 1006, 941, 878, 843, 734, 699 cm$^{-1}$; $^1$H NMR (400 MHz, CDCl$_3$) δ 7.48-7.46 (m, 2H), 7.39-7.35 (m, 3H), 5.49 (s, 1H), 5.31 (s, 1H), 4.42-4.47 (m, 1H), 4.36-4.35 (d, J=2.4 Hz, 2H), 4.18-4.11 (m, 1H), 3.54-3.49 (dd, J$_1$=14.3 Hz, J$_2$=9.9 Hz, 1H), 3.05-2.99 (dd, J$_1$=14.3 Hz, J$_2$=6.6 Hz, 1H), 2.79-2.70 (m, 1H), 2.65-2.56 (m, 2H), 2.39-2.25 (3H), 2.08-1.96 (m, 2H), 1.95-1.85 (m, 3H), 1.79-1.72 (m, 3H), 1.69-1.19 (m, 21H including singlets for 3H each at 1.42 and 1.36), 0.95-0.93 (dd, J$_1$=6.1 Hz, J$_2$=4.1 Hz, 7H), 0.85 (s, 3H), 0.83 (s, 3H); $^{13}$C NMR (100 MHz, CDCl$_3$) δ 131.1, 128.8, 128.6, 128.0, 103.4, 103.0, 89.4, 88.7, 81.4, 81.2, 74.1, 71.0, 59.7, 54.6, 53.4, 52.6, 52.2, 44.7, 44.2, 37.5, 37.2, 36.6, 34.6, 34.4, 31.3, 30.4, 30.3, 30.2, 26.3, 26.1, 24.8, 24.7, 24.7, 20.3, 20.1, 13.4, 12.9.

Example 12

Synthesis of ASR-isobu-SO$_2$-Ph-CH$_2$OC(O)NMe$_2$ (17)

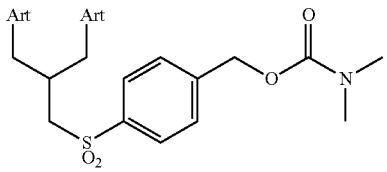

ASR-isobu-SO$_2$-Ph-CH$_2$OH 6 (20 mg, 0.026 mmol) was dissolved in anhydrous THF (1 mL) under argon at room temperature. To the solution was added dimethylcarbamyl chloride (5 μL, 0.052 mmol) and NaH (1.2 mg, 0.052 mmol) consecutively and the reaction was stirred at room temperature for 18 h. The reaction was quenched with sat. aq. sodium bicarbonate (1 mL) and extracted with dichloromethane (2×2 mL). The organic layer was dried with MgSO$_4$, filtered, and concentrated in vacuo. The crude product was purified by flash silica gel column chromatography (40% EtOAc/hexanes) to yield ASR-isobu-SO$_2$-Ph-CH$_2$OC(O)NMe$_2$ 17 (10 mg, 0.012 mmol, 48%) as an amorphous white solid. $^1$H NMR (400 MHz, CDCl$_3$) δ 8.02-8.00 (d, J=8.0 Hz, 2H), 7.50-7.48 (d, J=8.0 Hz, 2H), 5.48 (s, 1H), 5.34 (s, 1H), 5.18 (s, 2H), 4.45-4.43 (m, 1H), 4.14-4.10 (m, 1H), 3.63-3.58 (dd, J$_1$=14.4 Hz, J$_2$=7.2 Hz, 1H), 3.38-3.32 (dd, J$_1$=14.4 Hz, J$_2$=7.2 Hz, 1H), 2.95 (s, 6H), 2.71-2.65 (m, 1H), 2.58-2.50 (m, 21-1), 2.39-2.26 (m, 2H), 2.24-2.15 (m, 1H), 2.09-1.97 (m, 2H), 1.95-1.84 (m, 3H), 1.82-1.16 (m, 22H including singlets for 3H each at 1.43 and 1.35), 0.95-0.03 (m, 8H), 0.84-0.82 (m, 6H); $^{13}$C NMR (100 MHz, CDCl$_3$) δ 174.7, 142.7, 139.9, 128.4, 127.9, 103.3, 102.9, 89.5, 88.8, 81.3, 81.2, 77.2, 74.0, 71.0, 66.0, 58.9, 56.6, 52.5, 52.1, 44.6, 44.1, 37.4, 37.3, 36.7, 36.6, 34.6, 34.4, 31.2, 31.1, 30.7, 30.4, 26.2, 26.1, 24.8, 24.8, 24.7, 24.7, 20.3, 20.1, 13.3, 12.7.

The foregoing description is considered as illustrative only of the principles of the disclosure. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. Furthermore, since a number of modifications and changes will readily occur to those skilled in the art, it is not desired to limit the disclosure to the exact construction and process shown described above. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:
1. A compound of Formula I:

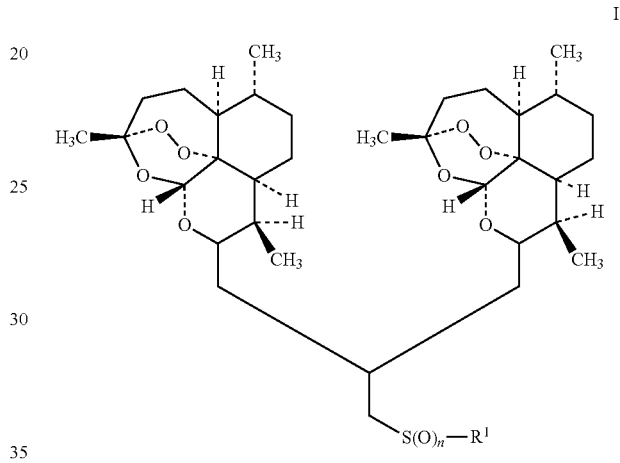

or a pharmaceutically acceptable salt or solvate thereof, wherein:
n is independently an integer from 0 to 2;
R$^1$ is independently hydrogen, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, or substituted or unsubstituted heteroarylalkyl, wherein R$^1$ is optionally independently substituted with 1 to 5 R$^2$ groups;
R$^2$ is independently hydrogen, halogen, nitro, cyano, hydroxyl, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, substituted or unsubstituted heteroarylalkyl, (CH$_2$)$_j$CN, (CH$_2$)$_j$OR$^3$, (CH$_2$)$_q$O(CH$_2$)$_j$OR$^3$, (CH$_2$)$_q$O(CH$_2$)$_t$O(CH$_2$)$_j$OR$^3$, (CH$_2$)$_q$O(CH$_2$)$_t$O (CH$_2$)$_u$O(CH$_2$)$_j$OR$^3$, (CH$_2$)$_j$C(O)R$^3$, (CH$_2$)$_j$C(O)OR$^3$, (CH$_2$)$_j$OC(O)R$^3$, (CH$_2$)$_j$NR$^4$R$^5$, (CH$_2$)$_j$C(O)NR$^4$R$^5$, (CH$_2$)$_j$OC(O)NR$^4$R$^5$, (CH$_2$)$_j$NR$^6$C(O)R$^3$, (CH$_2$)$_j$NR$^6$C (O)OR$^3$, (CH$_2$)$_j$NR$^6$C(O)NR$^4$R$^5$, —(CH$_2$)$_j$S(O)$_m$R$^7$, (CH$_2$)$_j$S(O)$_2$NR$^4$R$^5$, (CH$_2$)$_j$NR$^6$S(O)$_2$R$^7$, or (CH$_2$)$_j$OP (O)(OR$^7$)$_2$, wherein q is independently an integer from 0 to 20, and j, t, and u are each independently an integer from 0 to 6, and each m is independently an integer from 0 to 2, wherein R$^2$ is optionally independently substituted with 1 to 5 R$^8$ groups;

$R^3$, $R^4$, $R^5$, $R^6$, and $R^7$ are each independently hydrogen, substituted or unsubstituted alkyl, substituted or unsubstituted heteroalkyl, perfluoroalkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, or substituted or unsubstituted heteroarylalkyl, or $R^3$, $R^6$, and $R^7$ are as described above, and $R^4$ and $R^5$, together with the N atom to which they are attached, form substituted or unsubstituted heterocycloalkyl, or substituted or unsubstituted heteroaryl, wherein $R^3$, $R^4$, $R^5$, $R^6$, and $R^7$ are each optionally independently substituted with 1 to 5 $R^8$ groups; and $R^8$ is independently halogen, hydroxyl, cyano, nitro, alkyl, perfluoroalkyl, oxo, $NH_2$, NH(alkyl), N(alkyl)$_2$, O-alkyl, S-alkyl, aryl, arylalkyl, heteroaryl or heteroarylalkyl.

2. The compound of claim 1, wherein:

n is independently 2;

$R^1$ is independently substituted or unsubstituted ($C_1$-$C_{20}$) alkyl, substituted or unsubstituted ($C_1$-$C_{20}$)heteroalkyl, substituted or unsubstituted ($C_3$-$C_7$)cycloalkyl, substituted or unsubstituted ($C_3$-$C_7$)heterocycloalkyl, substituted or unsubstituted phenyl, substituted or unsubstituted biphenyl, substituted or unsubstituted naphthyl, substituted or unsubstituted benzyl, substituted or unsubstituted pyrrolyl, substituted or unsubstituted pyrazolyl, substituted or unsubstituted imidazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzimidazolyl, substituted or unsubstituted benzofuryl, substituted or unsubstituted benzothienyl, substituted or unsubstituted benzoxazolyl, substituted or unsubstituted benzoisooxazolyl, substituted or unsubstituted benzthiazolyl, substituted or unsubstituted quinolinyl, substituted or unsubstituted isoquinolinyl, substituted or unsubstituted phthalazinyl, substituted or unsubstituted quinazolinyl, or substituted or unsubstituted quinoxalinyl;

$R^2$ is independently hydrogen, halogen, nitro, cyano, hydroxyl, substituted or unsubstituted ($C_1$-$C_6$)alkyl, substituted or unsubstituted ($C_1$-$C_6$)heteroalkyl, perfluoroalkyl, substituted or unsubstituted ($C_3$-$C_7$)cycloalkyl, substituted or unsubstituted ($C_3$-$C_7$)heterocycloalkyl, substituted or unsubstituted phenyl, substituted or unsubstituted biphenyl, substituted or unsubstituted naphthyl, substituted or unsubstituted benzyl, substituted or unsubstituted pyrrolyl, substituted or unsubstituted pyrazolyl, substituted or unsubstituted imidazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzimidazolyl, substituted or unsubstituted benzofuryl, substituted or unsubstituted benzothienyl, substituted or unsubstituted benzoxazolyl, substituted or unsubstituted benzoisooxazolyl, substituted or unsubstituted benzthiazolyl, substituted or unsubstituted quinolinyl, substituted or unsubstituted isoquinolinyl, substituted or unsubstituted phthalazinyl, substituted or unsubstituted quinazolinyl, substituted or unsubstituted quinoxalinyl, —(CH$_2$)$_j$CN, —(CH$_2$)$_j$OR$^3$, —(CH$_2$)$_q$O(CH$_2$)$_j$OR$^3$, —(CH$_2$)$_q$O(CH$_2$)$_t$O(CH$_2$)$_j$OR$^3$, —(CH$_2$)$_q$O(CH$_2$)$_t$O(CH$_2$)$_u$O(CH$_2$)$_j$OR$^3$, —(CH$_2$)$_j$C(O)R$^3$, —(CH$_2$)$_j$C(O)OR$^3$, —(CH$_2$)$_j$OC(O)R$^3$, —(CH$_2$)$_j$NR$^4$R$^5$, —(CH$_2$)$_j$C(O)NR$^4$R$^5$, —(CH$_2$)$_j$OC(O)NR$^4$R$^5$, —(CH$_2$)$_j$NR$^6$C(O)R$^3$, —(CH$_2$)$_j$NR$^6$C(O)OR$^3$, —(CH$_2$)$_j$NR$^6$C(O)NR$^4$R$^5$, —(CH$_2$)$_j$S(O)$_m$R$^7$, —(CH$_2$)$_j$S(O)$_2$NR$^4$R$^5$, —(CH$_2$)$_j$NR$^6$S(O)$_2$R$^7$, or —(CH$_2$)$_j$OP(O)(OR$^7$)$_2$;

$R^3$, $R^4$, $R^5$, $R^6$, and $R^7$ are each independently hydrogen, substituted or unsubstituted ($C_1$-$C_6$)alkyl, substituted or unsubstituted ($C_1$-$C_6$)heteroalkyl, perfluoroalkyl, substituted or unsubstituted ($C_3$-$C_7$)cycloalkyl, substituted or unsubstituted ($C_3$-$C_7$)heterocycloalkyl, substituted or unsubstituted phenyl, substituted or unsubstituted biphenyl, substituted or unsubstituted naphthyl, substituted or unsubstituted benzyl, substituted or unsubstituted pyrrolyl, substituted or unsubstituted pyrazolyl, substituted or unsubstituted imidazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzimidazolyl, substituted or unsubstituted benzofuryl, substituted or unsubstituted benzothienyl, substituted or unsubstituted benzoxazolyl, substituted or unsubstituted benzoisooxazolyl, substituted or unsubstituted benzthiazolyl, substituted or unsubstituted quinolinyl, substituted or unsubstituted isoquinolinyl, substituted or unsubstituted phthalazinyl, substituted or unsubstituted quinazolinyl, or substituted or unsubstituted quinoxalinyl, or $R^3$, $R^6$, and $R^7$ are as described above, and $R^4$ and $R^5$, together with the N atom to which they are attached, form substituted or unsubstituted pyrrolidinyl, substituted or unsubstituted imidazolidinyl, substituted or unsubstituted piperidinyl, substituted or unsubstituted piperazinyl, substituted or unsubstituted morpholinyl, substituted or unsubstituted thiomorpholinyl, substituted or unsubstituted pyrrolyl, or substituted or unsubstituted imidazolyl; and $R^8$ is independently halogen, hydroxyl, cyano, nitro, perfluoroalkyl, oxo, $NH_2$, NH(($C_1$-$C_6$)alkyl), N(($C_1$-$C_6$)alkyl)$_2$, O($C_1$-$C_6$)alkyl, S($C_1$-$C_6$)alkyl, phenyl, biphenyl, naphthyl, benzyl, pyrrolyl, pyrazolyl, imidazolyl, furyl, thienyl, oxazolyl, isooxazolyl, thiazolyl, pyridinyl, pyridazinyl, pyrimidinyl, pyrazinyl, indolyl, indazolyl, benzimidazolyl, benzofuryl, benzothienyl, benzoxazolyl, benzoisooxazolyl, benzthiazolyl, quinolinyl, isoquinolinyl, phthalazinyl, quinazolinyl, or quinoxalinyl.

3. The compound of claim 2, wherein:

$R^1$ is independently substituted or unsubstituted ($C_1$-$C_{20}$) alkyl; and $R^2$ is independently hydrogen, halogen, nitro, cyano, hydroxyl, substituted or unsubstituted ($C_1$-$C_6$)alkyl, substituted or unsubstituted ($C_1$-$C_6$)heteroalkyl, perfluoroalkyl, substituted or unsubstituted (C$_3$-C$_7$)cycloalkyl, substituted or unsubstituted (C$_3$-C$_7$)heterocycloalkyl.

4. The compound of claim 2, wherein:
R$^1$ is independently substituted or unsubstituted (C$_1$-C$_{20}$) alkyl; and
R$^2$ is independently substituted or unsubstituted phenyl, substituted or unsubstituted biphenyl, substituted or unsubstituted naphthyl, substituted or unsubstituted benzyl, substituted or unsubstituted pyrrolyl, substituted or unsubstituted pyrazolyl, substituted or unsubstituted imidazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzimidazolyl, substituted or unsubstituted benzofuryl, substituted or unsubstituted benzothienyl, substituted or unsubstituted benzoxazolyl, substituted or unsubstituted benzoisooxazolyl, substituted or unsubstituted benzthiazolyl, substituted or unsubstituted quinolinyl, substituted or unsubstituted isoquinolinyl, substituted or unsubstituted phthalazinyl, substituted or unsubstituted quinazolinyl, or substituted or unsubstituted quinoxalinyl.

5. The compound of claim 2, wherein:
R$^1$ is independently substituted or unsubstituted (C$_1$-C$_{20}$) alkyl; and
R$^2$ is independently —(CH$_2$)$_j$CN, —(CH$_2$)$_j$OR$^3$, —(CH$_2$)$_q$O(CH$_2$)$_j$OR$^3$, —(CH$_2$)$_q$O(CH$_2$)$_t$O(CH$_2$)$_j$OR$^3$, —(CH$_2$)$_q$ O(CH$_2$)$_t$O(CH$_2$)$_u$O(CH$_2$)$_j$OR$^3$, —(CH$_2$)$_j$C(O)R$^3$, —(CH$_2$)$_j$C(O)OR$^3$, —(CH$_2$)$_j$OC(O)R$^3$, —(CH$_2$)$_j$NR$^4$R$^5$, —(CH$_2$)$_j$C(O)NR$^4$R$^5$, —(CH$_2$)$_j$OC(O)NR$^4$R$^5$, —(CH$_2$)$_j$NR$^6$C(O)R$^3$, —(CH$_2$)$_j$NR$^6$C(O)OR$^3$, —(CH$_2$)$_j$NR$^6$C(O)NR$^4$R$^5$, —(CH$_2$)$_j$S(O)$_m$R$^7$, —(CH$_2$)$_j$S(O)$_2$NR$^4$R$^5$, —(CH$_2$)$_j$NR$^6$S(O)$_2$R$^7$, or —(CH$_2$)$_j$OP(O)(OR$^7$)$_2$.

6. The compound of claim 5, wherein R$^2$ is independently —(CH$_2$)$_j$OR$^3$, —(CH$_2$)$_q$O(CH$_2$)$_j$OR$^3$, —(CH$_2$)$_q$O(CH$_2$)$_t$O(CH$_2$)$_j$OR$^3$, or —(CH$_2$)$_q$O(CH$_2$)$_t$O(CH$_2$)$_u$O(CH$_2$)$_j$OR$^3$.

7. The compound of claim 6, wherein R$^3$ is hydrogen.

8. The compound of claim 2, wherein:
R$^1$ is independently substituted or unsubstituted phenyl; and
R$^2$ is independently hydrogen, halogen, nitro, cyano, hydroxyl, substituted or unsubstituted (C$_1$-C$_6$)alkyl, substituted or unsubstituted (C$_1$-C$_6$)heteroalkyl, perfluoroalkyl, substituted or unsubstituted (C$_3$-C$_7$)cycloalkyl, or substituted or unsubstituted (C$_3$-C$_7$)heterocycloalkyl.

9. The compound of claim 2, wherein:
R$^1$ is independently substituted or unsubstituted phenyl; and
R$^2$ is independently substituted or unsubstituted phenyl, substituted or unsubstituted biphenyl, substituted or unsubstituted naphthyl, substituted or unsubstituted benzyl, substituted or unsubstituted pyrrolyl, substituted or unsubstituted pyrazolyl, substituted or unsubstituted imidazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzimidazolyl, substituted or unsubstituted benzofuryl, substituted or unsubstituted benzothienyl, substituted or unsubstituted benzoxazolyl, substituted or unsubstituted benzoisooxazolyl, substituted or unsubstituted benzthiazolyl, substituted or unsubstituted quinolinyl, substituted or unsubstituted isoquinolinyl, substituted or unsubstituted phthalazinyl, substituted or unsubstituted quinazolinyl, or substituted or unsubstituted quinoxalinyl.

10. The compound of claim 2, wherein:
R$^1$ is independently substituted or unsubstituted phenyl; and
R$^2$ is independently —(CH$_2$)$_j$CN, —(CH$_2$)$_j$OR$^3$, —(CH$_2$)$_q$O(CH$_2$)$_j$OR$^3$, —(CH$_2$)$_q$O(CH$_2$)$_t$O(CH$_2$)$_j$OR$^3$, —(CH$_2$)$_q$ O(CH$_2$)$_t$O(CH$_2$)$_u$O(CH$_2$)$_j$OR$^3$, —(CH$_2$)$_j$C(O)R$^3$, —(CH$_2$)$_j$C(O)OR$^3$, —(CH$_2$)$_j$OC(O)R$^3$, —(CH$_2$)$_j$NR$^4$R$^5$, —(CH$_2$)$_j$C(O)NR$^4$R$^5$, —(CH$_2$)$_j$OC(O)NR$^4$R$^5$, —(CH$_2$)$_j$NR$^6$C(O)R$^3$, —(CH$_2$)$_j$NR$^6$C(O)OR$^3$, —(CH$_2$)$_j$NR$^6$C(O)NR$^4$R$^5$, —(CH$_2$)$_j$S(O)$_m$R$^7$, —(CH$_2$)$_j$S(O)$_2$NR$^4$R$^5$, —(CH$_2$)$_j$NR$^6$S(O)$_2$R$^7$, or —(CH$_2$)$_j$OP(O)(OR$^7$)$_2$.

11. The compound of claim 10, wherein R$^2$ is independently —(CH$_2$)$_j$OR$^3$, —(CH$_2$)$_q$O(CH$_2$)$_j$OR$^3$, —(CH$_2$)$_q$O(CH$_2$)$_t$O(CH$_2$)$_j$OR$^3$, or —(CH$_2$)$_q$O(CH$_2$)$_t$O(CH$_2$)$_u$O(CH$_2$)$_j$OR$^3$.

12. The compound of claim 11, wherein R$^3$ is hydrogen; R$^4$ and R$^5$ are (C$_1$-C$_6$)alkyl; and R$^7$ is (C$_1$-C$_6$)alkyl, or phenyl.

13. The compound of claim 10, wherein R$^2$ is independently —(CH$_2$)$_j$OR$^3$; R$^3$ is arylalkyl; and R$^8$ is halogen.

14. The compound of claim 1, having formula:

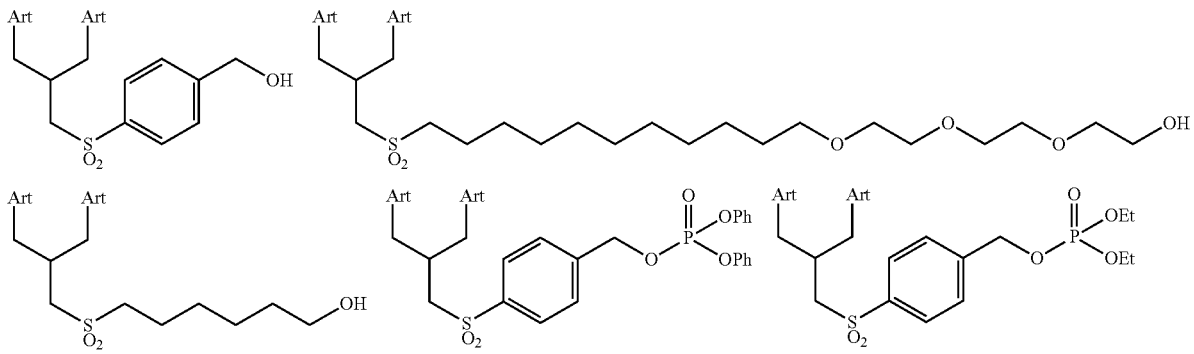

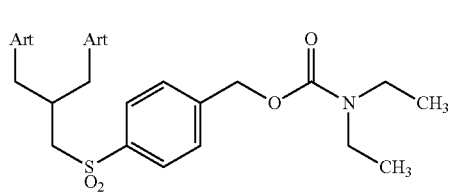 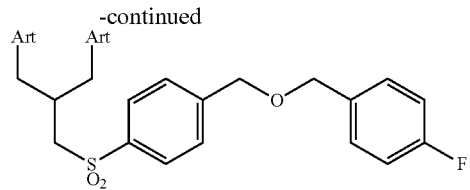

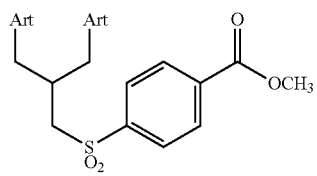 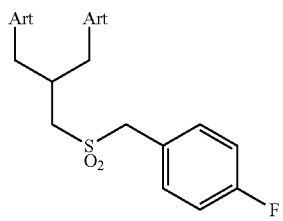 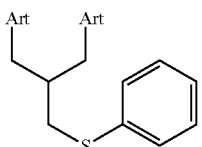 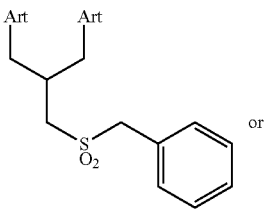

or

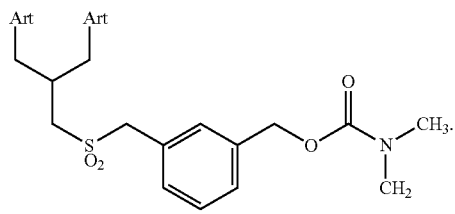

15. A method of preparing the compound of Formula I of claim 1, comprising the steps of:
a) reacting the compound of Formula II with R¹SH and base to provide the sulfide compound of Formula I; and
b) optionally treating the sulfide compound of Formula I with an oxidizing agent to provide the sulfoxide and/or sulfone compound of Formula I:

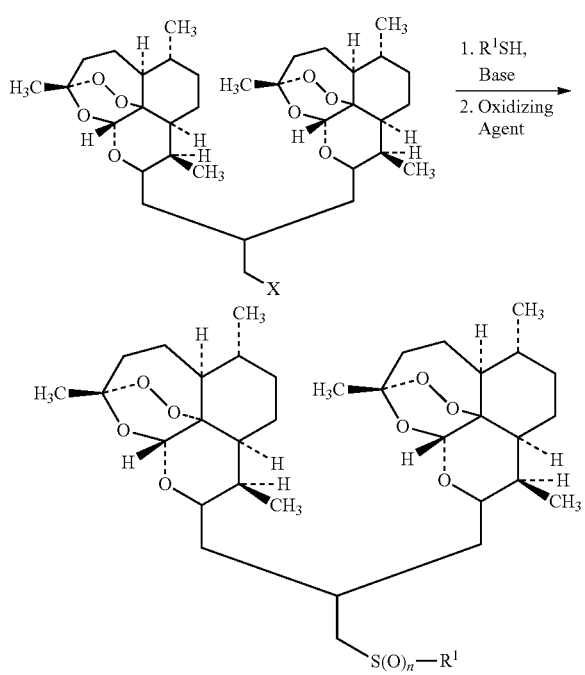

wherein X is a leaving group.

16. The method of claim 15, wherein X is halogen, mesylate, tosylate or triflate; and the base is 1,8-diazabicyclo[5.4.0]undec-7-ene (DBU), sodium hydride, or pyridine.

17. The compound of Formula I, prepared by the method of claim 15.

18. A pharmaceutical composition comprising a pharmaceutically acceptable excipient and a compound of Formula I of claim 1.

19. A method of treating cancer in a subject in need of such treatment, the method comprising the steps of administering to the subject a therapeutically effective amount of a compound of Formula I of claim 1.

20. The method of claim 19, wherein the cancer is leukemia, non-small cell lung cancer, colon cancer, central nervous system cancer, melanoma cancer, ovarian cancer, renal cancer, prostate cancer, and breast cancer.

21. A method of treating malaria in a subject in need of such treatment, the method comprising the steps of administering to the subject a therapeutically effective amount of a compound of Formula I of claim 1.

* * * * *